(12) United States Patent
Patti et al.

(10) Patent No.: US 8,475,798 B2
(45) Date of Patent: Jul. 2, 2013

(54) MONOCLONAL ANTIBODIES RECOGNIZING A COAGULASE-NEGATIVE STAPHYLOCOCCAL PROTEIN

(75) Inventors: Joseph M. Patti, Alpharetta, GA (US); Jeff T. Hutchins, Cumming, GA (US); Andrea Hall, Acworth, GA (US); Linda Santos, San Antonio, TX (US); Maria Bowden, Sugar Land, TX (US); Magnus Hook, Houston, TX (US)

(73) Assignees: Inhibitex, Inc., Alpharetta, GA (US); The Texas A&M University System, College Station, TX (US)

( * ) Notice: Subject to any disclaimer, the term of this patent is extended or adjusted under 35 U.S.C. 154(b) by 757 days.

(21) Appl. No.: 11/917,435

(22) PCT Filed: Jun. 16, 2006

(86) PCT No.: PCT/US2006/023590
§ 371 (c)(1),
(2), (4) Date: Nov. 16, 2009

(87) PCT Pub. No.: WO2006/138627
PCT Pub. Date: Dec. 28, 2006

(65) Prior Publication Data
US 2010/0183623 A1 Jul. 22, 2010

Related U.S. Application Data

(60) Provisional application No. 60/690,940, filed on Jun. 16, 2005.

(51) Int. Cl.
*A61K 39/40* (2006.01)
*A61K 39/00* (2006.01)
*A61K 39/395* (2006.01)
*G01N 33/569* (2006.01)

(52) U.S. Cl.
USPC ............... 424/150.1; 424/141.1; 424/142.1; 424/130.1; 424/139.1; 424/165.1; 435/975; 435/7.33; 530/388.4; 530/388.1; 530/388.15

(58) Field of Classification Search
None
See application file for complete search history.

(56) References Cited

U.S. PATENT DOCUMENTS

| | | |
|---|---|---|
| 6,008,341 A | 12/1999 | Foster et al. |
| 6,177,084 B1 | 1/2001 | Foster et al. |
| 6,288,214 B1 | 9/2001 | Hook et al. |
| 6,635,473 B1 | 10/2003 | Foster |
| 6,680,195 B1 | 1/2004 | Patti et al. |
| 6,685,943 B1 | 2/2004 | Hook et al. |
| 6,692,739 B1 | 2/2004 | Patti et al. |
| 6,703,025 B1 | 3/2004 | Patti et al. |
| 6,797,492 B2 | 9/2004 | Daugherty et al. |
| 6,841,154 B2 | 1/2005 | Foster et al. |
| 6,979,446 B2 | 12/2005 | Patti et al. |
| 6,994,855 B1 | 2/2006 | Foster et al. |
| 7,045,131 B2 | 5/2006 | Patti et al. |
| 2004/0006209 A1* | 1/2004 | Patti et al. ............... 530/350 |
| 2004/0038327 A1 | 2/2004 | Foster et al. |

OTHER PUBLICATIONS

Kabat et al. J. Exp. Med. 164: 642-654, 1986.*
Webster's II New Riverside University Dictionary, The Riverside Publishing Company, p. 933, 1984.*
Illustrated Stedman's Medical Dictionary, 24th Ed, Williams and Wilkins, Baltimore, p. 707, 1982.*

* cited by examiner

*Primary Examiner* — S. Devi
(74) *Attorney, Agent, or Firm* — B. Aaron Schulman, Esq.; Stites & Harbison, PLLC

(57) ABSTRACT

Monoclonal antibodies which can bind to the SdrF protein of *Staphylococcus epidermidis* are provided which can be useful in the treatment and protection against infection from staphylococcal bacteria such as *Staphylococcus epidermidis*. The monoclonal antibodies of the invention are advantageous in that they can also recognize binding domains and subdomains of the *S. epidermidis* SdrF protein in addition to the protein itself. Suitable compositions and passive vaccines based on the monoclonal antibodies of the invention, as well as methods for their use, are also provided.

17 Claims, 4 Drawing Sheets

SEQUENCE LISTING

<160> NUMBER OF SEQ ID NOS: 34

<210> SEQ ID NO 1
<211> LENGTH: 1878
<212> TYPE: DNA
<213> ORGANISM: Staphylococcus epidermidis

<400> SEQUENCE: 1

```
gctgaagaca atcaattaga atcagcttca aaagaagaac agaaaggtag tcgtgataat      60
gaaaactcaa aacttaatca agtcgattta gacaacggat cacatagttc tgagaaaaca     120
acaaatgtaa acaatgcaac tgaagtaaaa aaagttgaag caccaacgac aagtgacgta     180
tctaagccta aagctaatga agcagtagtg acgaatgagt caactaaacc aaaaacaaca     240
gaagcaccaa ctgttaatga ggaatcaata gctgaaacac ccaaaacctc aactacacaa     300
caagattcga ctgagaagaa taatccatct ttaaaagata atttaaattc atcctcaacg     360
acatctaaag aaagtaaaac agacgaacat tctactaagc aagctcaaat gtctactaat     420
aaatcaaatt tagacacaaa tgactctcca actcaaagtg agaaaacttc atcacaagca     480
aataacgaca gtacagataa tcagtcagca ccttctaaac aattagattc aaaaccatca     540
gaacaaaaag tatataaaac aaaatttaat gatgaaccta ctcaagatgt tgaacacacg     600
acaactaaat taaaacacc ttctgtttca acagatagtt cagtcaatga taagcaagat     660
tacacacgaa gtgctgtagc tagtttaggt gttgattcta atgaaacaga agcaattaca     720
aatgcagtta gagacaattt agatttaaaa gctgcatcta gagaacaaat caatgaagca     780
atcattgctg aagcactaaa aaaagacttt tctaaccctg attatggtgt cgatacgcca     840
ttagctctaa acagatctca atcaaaaaat tcaccacata agagtgcaag tccacgcatg     900
aatttaatga gtttagctgc tgagcctaat agtggtaaaa atgtgaatga taagttaaa      960 atcacaaacc ctacgctttc acttaataag agtaataatc acgctaataa cgtaatatgg    1020
ccaacaagta acgaacaatt taatttaaaa gcaaattatg aattagatga cagcataaaa    1080
gagggagata cttttactat taagtatggt cagtatatta gaccgggtgg tttagaactt    1140
cctgcaataa aaactcaact acgtagtaag gatggctcta ttgtagctaa tggtgtatat    1200
gataaaacta caaatacgac gacttataca tttactaact atgttgatca atatcaaaat    1260
attacaggta gttttgattt aattgcgacg cctaagaggg aaacagcaat taaggataat    1320
cagaattatc ctatggaagt gacgattgct aacgaagtag tcaaaaaaga cttcattgtg    1380
gattatggta ataaaaagga caatacaact acagcagcgg tagcaaatgt ggataatgta    1440
aataataaac ataacgaagt tgtttatcta aaccaaaata accaaaaccc taaatatgct    1500
aaatatttct caacagtaaa aaatggtgaa tttataccag gtgaagtgaa agtttacgaa    1560
gtgacggata ccaatgcgat ggtagatagc ttcaatcctg atttaaatag ttctaatgta    1620
aaagatgtga caagtcaatt tgcacctaaa gtaagtgcag atggtactag agttgatatc    1680
```

```
aattttgcta gaagtatggc aaatggtaaa aagtatattg taactcaagc agtgagacca    1740
acgggaactg aaatgttta  taccgaatat tggttaacaa gagatggtac taccaataca    1800 aatgatttt  accgtggaac gaagtctaca acggtgactt atctcaatgg ttcttcaaca    1860
gcacaggggg ataatcct                                                  1878
```

<210> SEQ ID NO 2
<211> LENGTH: 626
<212> TYPE: PRT
<213> ORGANISM: Staphylococcus epidermidis

<400> SEQUENCE: 2

```
Ala Glu Asp Asn Gln Leu Glu Ser Ala Ser Lys Glu Glu Gln Lys Gly
1               5                   10                  15

Ser Arg Asp Asn Glu Asn Ser Lys Leu Asn Gln Val Asp Leu Asp Asn
            20                  25                  30

Gly Ser His Ser Ser Glu Lys Thr Thr Asn Val Asn Asn Ala Thr Glu
        35                  40                  45

Val Lys Lys Val Glu Ala Pro Thr Thr Ser Asp Val Ser Lys Pro Lys
    50                  55                  60

Ala Asn Glu Ala Val Val Thr Asn Glu Ser Thr Lys Pro Lys Thr Thr
65                  70                  75                  80

Glu Ala Pro Thr Val Asn Glu Glu Ser Ile Ala Glu Thr Pro Lys Thr
                85                  90                  95

Ser Thr Thr Gln Gln Asp Ser Thr Glu Lys Asn Asn Pro Ser Leu Lys
            100                 105                 110

Asp Asn Leu Asn Ser Ser Ser Thr Ser Lys Glu Ser Lys Thr Asp
        115                 120                 125

Glu His Ser Thr Lys Gln Ala Gln Met Ser Thr Asn Lys Ser Asn Leu
    130                 135                 140

Asp Thr Asn Asp Ser Pro Thr Gln Ser Glu Lys Thr Ser Ser Gln Ala
145                 150                 155                 160

Asn Asn Asp Ser Thr Asp Asn Gln Ser Ala Pro Ser Lys Gln Leu Asp
                165                 170                 175

Ser Lys Pro Ser Glu Gln Lys Val Tyr Lys Thr Lys Phe Asn Asp Glu
            180                 185                 190

Pro Thr Gln Asp Val Glu His Thr Thr Thr Lys Leu Lys Thr Pro Ser
        195                 200                 205

Val Ser Thr Asp Ser Ser Val Asn Asp Lys Gln Asp Tyr Thr Arg Ser
    210                 215                 220

Ala Val Ala Ser Leu Gly Val Asp Ser Asn Glu Thr Glu Ala Ile Thr
225                 230                 235                 240

Asn Ala Val Arg Asp Asn Leu Asp Leu Lys Ala Ala Ser Arg Glu Gln
                245                 250                 255

Ile Asn Glu Ala Ile Ile Ala Glu Ala Leu Lys Lys Asp Phe Ser Asn
            260                 265                 270

Pro Asp Tyr Gly Val Asp Thr Pro Leu Ala Leu Asn Arg Ser Gln Ser
        275                 280                 285

Lys Asn Ser Pro His Lys Ser Ala Ser Pro Arg Met Asn Leu Met Ser
    290                 295                 300

Leu Ala Ala Glu Pro Asn Ser Gly Lys Asn Val Asn Asp Lys Val Lys
305                 310                 315                 320

Ile Thr Asn Pro Thr Leu Ser Leu Asn Lys Ser Asn Asn His Ala Asn
                325                 330                 335
```

```
Asn Val Ile Trp Pro Thr Ser Asn Glu Gln Phe Asn Leu Lys Ala Asn
            340                 345                 350

Tyr Glu Leu Asp Asp Ser Ile Lys Glu Gly Asp Thr Phe Thr Ile Lys
            355                 360                 365

Tyr Gly Gln Tyr Ile Arg Pro Gly Gly Leu Glu Leu Pro Ala Ile Lys
    370                 375                 380

Thr Gln Leu Arg Ser Lys Asp Gly Ser Ile Val Ala Asn Gly Val Tyr
385                 390                 395                 400

Asp Lys Thr Thr Asn Thr Thr Thr Tyr Thr Phe Thr Asn Tyr Val Asp
                405                 410                 415

Gln Tyr Gln Asn Ile Thr Gly Ser Phe Asp Leu Ile Ala Thr Pro Lys
            420                 425                 430

Arg Glu Thr Ala Ile Lys Asp Asn Gln Asn Tyr Pro Met Glu Val Thr
            435                 440                 445

Ile Ala Asn Glu Val Val Lys Lys Asp Phe Ile Val Asp Tyr Gly Asn
    450                 455                 460

Lys Lys Asp Asn Thr Thr Thr Ala Ala Val Ala Asn Val Asp Asn Val
465                 470                 475                 480

Asn Asn Lys His Asn Glu Val Val Tyr Leu Asn Gln Asn Asn Gln Asn
                485                 490                 495

Pro Lys Tyr Ala Lys Tyr Phe Ser Thr Val Lys Asn Gly Glu Phe Ile
            500                 505                 510

Pro Gly Glu Val Lys Val Tyr Glu Val Thr Asp Thr Asn Ala Met Val
            515                 520                 525

Asp Ser Phe Asn Pro Asp Leu Asn Ser Ser Asn Val Lys Asp Val Thr
    530                 535                 540

Ser Gln Phe Ala Pro Lys Val Ser Ala Asp Gly Thr Arg Val Asp Ile
545                 550                 555                 560

Asn Phe Ala Arg Ser Met Ala Asn Gly Lys Lys Tyr Ile Val Thr Gln
                565                 570                 575

Ala Val Arg Pro Thr Gly Thr Gly Asn Val Tyr Thr Glu Tyr Trp Leu
            580                 585                 590

Thr Arg Asp Gly Thr Thr Asn Thr Asn Asp Phe Tyr Arg Gly Thr Lys
            595                 600                 605

Ser Thr Thr Val Thr Tyr Leu Asn Gly Ser Ser Thr Ala Gln Gly Asp
    610                 615                 620

Asn Pro
625

<210> SEQ ID NO 3
<211> LENGTH: 1917
<212> TYPE: DNA
<213> ORGANISM: Staphylococcus epidermidis

<400> SEQUENCE: 3
atgagaggat cgcatcacca tcaccatcac ggatccgctg aagacaatca attagaatca      60
gcttcaaaag aagaacagaa aggtagtcgt gataatgaaa actcaaaact taatcaagtc     120
gatttagaca acggatcaca tagttctgag aaaacaacaa atgtaaacaa tgcaactgaa     180
gtaaaaaaag ttgaagcacc aacgacaagt gacgtatcta agcctaaagc taatgaagca     240
gtagtgacga atgagtcaac taaaccaaaa acaacagaag caccaactgt taatgaggaa     300
tcaatagctg aaacacccaa aacctcaact acacaacaag attcgactga agaataat      360 ccatctttaa aagataattt aaattcatcc tcaacgacat ctaagaaag taaacagac      420 gaacattcta ctaagcaagc tcaaatgtct actaataaat caatttaga cacaaatgac     480
```

-continued

```
tctccaactc aaagtgagaa aacttcatca caagcaaata acgacagtac agataatcag    540
tcagcacctt ctaaacaatt agattcaaaa ccatcagaac aaaaagtata aaaacaaaa     600
tttaatgatg aacctactca agatgttgaa cacacgacaa ctaaattaaa aacaccttct    660
gtttcaacag atagttcagt caatgataag caagattaca cacgaagtgc tgtagctagt    720
ttaggtgttg attctaatga acagaagca attacaaatg cagttagaga caatttagat     780
ttaaaagctg catctagaga acaaatcaat gaagcaatca ttgctgaagc actaaaaaaa    840
gactttccta accctgatta tggtgtcgat acgccattag ctctaaacag atctcaatca    900
aaaaattcac cacataagag tgcaagtcca cgcatgaatt taatgagttt agctgctgag    960
cctaatagtg gtaaaaatgt gaatgataaa gttaaaatca caaaccctac gctttcactt   1020
aataagagta ataatcacgc taataacgta atatggccaa caagtaacga acaatttaat   1080
ttaaaagcaa attatgaatt agatgacagc ataaaagagg gagatacttt tactattaag   1140
tatggtcagt atattagacc gggtggttta gaacttcctg caataaaaac tcaactacgt   1200
agtaaggatg gctctattgt agctaatggt gtatatgata aaactacaaa tacgacgact   1260
tatacattta ctaactatgt tgatcaatat caaaatatta caggtagttt tgatttaatt   1320
gcgacgccta agagggaaac agcaattaag gataatcaga attatcctat ggaagtgacg   1380
attgctaacg aagtagtcaa aaaagacttc attgtggatt atggtaataa aaaggacaat   1440
acaactacag cagcggtagc aaatgtggat aatgtaaata ataaacataa cgaagttgtt   1500
tatctaaacc aaaataacca aaaccctaaa tatgctaaat atttctcaac agtaaaaaat   1560
ggtgaattta taccaggtga agtgaaagtt tacgaagtga cggataccaa tgcgatggta   1620
gatagcttca atcctgattt aaatagttct aatgtaaaag atgtgacaag tcaatttgca   1680
cctaaagtaa gtgcagatgg tactagagtt gatatcaatt ttgctagaag tatggcaaat   1740
ggtaaaaagt atattgtaac tcaagcagtg agaccaacgg gaactggaaa tgtttatacc   1800
gaatattggt taacaagaga tggtactacc aatacaaatg atttttaccg tggaacgaag   1860
tctacaacgg tgacttatct caatggttct tcaacagcac agggggataa tccttga       1917
```

<210> SEQ ID NO 4
<211> LENGTH: 638
<212> TYPE: PRT
<213> ORGANISM: Staphylococcus epidermidis

<400> SEQUENCE: 4

```
Met Arg Gly Ser His His His His His His Gly Ser Ala Glu Asp Asn
1               5                   10                  15

Gln Leu Glu Ser Ala Ser Lys Glu Glu Gln Lys Gly Ser Arg Asp Asn
            20                  25                  30

Glu Asn Ser Lys Leu Asn Gln Val Asp Leu Asp Asn Gly Ser His Ser
        35                  40                  45

Ser Glu Lys Thr Thr Asn Val Asn Asn Ala Thr Glu Val Lys Lys Val
    50                  55                  60

Glu Ala Pro Thr Thr Ser Asp Val Ser Lys Pro Lys Ala Asn Glu Ala
65                  70                  75                  80

Val Val Thr Asn Glu Ser Thr Lys Pro Lys Thr Thr Glu Ala Pro Thr
                85                  90                  95

Val Asn Glu Glu Ser Ile Ala Glu Thr Pro Lys Thr Ser Thr Thr Gln
            100                 105                 110

Gln Asp Ser Thr Glu Lys Asn Asn Pro Ser Leu Lys Asp Asn Leu Asn
        115                 120                 125
```

```
Ser Ser Ser Thr Thr Ser Lys Glu Ser Lys Thr Asp Glu His Ser Thr
    130                 135                 140

Lys Gln Ala Gln Met Ser Thr Asn Lys Ser Asn Leu Asp Thr Asn Asp
145                 150                 155                 160

Ser Pro Thr Gln Ser Glu Lys Thr Ser Ser Gln Ala Asn Asn Asp Ser
                    165                 170                 175

Thr Asp Asn Gln Ser Ala Pro Ser Lys Gln Leu Asp Ser Lys Pro Ser
                180                 185                 190

Glu Gln Lys Val Tyr Lys Thr Lys Phe Asn Asp Glu Pro Thr Gln Asp
            195                 200                 205

Val Glu His Thr Thr Thr Lys Leu Lys Thr Pro Ser Val Ser Thr Asp
        210                 215                 220

Ser Ser Val Asn Asp Lys Gln Asp Tyr Thr Arg Ser Ala Val Ala Ser
225                 230                 235                 240

Leu Gly Val Asp Ser Asn Glu Thr Glu Ala Ile Thr Asn Ala Val Arg
                    245                 250                 255

Asp Asn Leu Asp Leu Lys Ala Ala Ser Arg Glu Gln Ile Asn Glu Ala
                260                 265                 270

Ile Ile Ala Glu Ala Leu Lys Lys Asp Phe Ser Asn Pro Asp Tyr Gly
            275                 280                 285

Val Asp Thr Pro Leu Ala Leu Asn Arg Ser Gln Ser Lys Asn Ser Pro
        290                 295                 300

His Lys Ser Ala Ser Pro Arg Met Asn Leu Met Ser Leu Ala Ala Glu
305                 310                 315                 320

Pro Asn Ser Gly Lys Asn Val Asn Asp Lys Val Lys Ile Thr Asn Pro
                    325                 330                 335

Thr Leu Ser Leu Asn Lys Ser Asn Asn His Ala Asn Asn Val Ile Trp
                340                 345                 350

Pro Thr Ser Asn Glu Gln Phe Asn Leu Lys Ala Asn Tyr Glu Leu Asp
            355                 360                 365

Asp Ser Ile Lys Glu Gly Asp Thr Phe Thr Ile Lys Tyr Gly Gln Tyr
        370                 375                 380

Ile Arg Pro Gly Gly Leu Glu Leu Pro Ala Ile Lys Thr Gln Leu Arg
385                 390                 395                 400

Ser Lys Asp Gly Ser Ile Val Ala Asn Gly Val Tyr Asp Lys Thr Thr
                    405                 410                 415

Asn Thr Thr Thr Tyr Thr Phe Thr Asn Tyr Val Asp Gln Tyr Gln Asn
                420                 425                 430

Ile Thr Gly Ser Phe Asp Leu Ile Ala Thr Pro Lys Arg Glu Thr Ala
            435                 440                 445

Ile Lys Asp Asn Gln Asn Tyr Pro Met Glu Val Thr Ile Ala Asn Glu
        450                 455                 460

Val Val Lys Lys Asp Phe Ile Val Asp Tyr Gly Asn Lys Lys Asp Asn
465                 470                 475                 480

Thr Thr Thr Ala Ala Val Ala Asn Val Asp Asn Val Asn Asn Lys His
                    485                 490                 495

Asn Glu Val Val Tyr Leu Asn Gln Asn Asn Gln Asn Pro Lys Tyr Ala
                500                 505                 510

Lys Tyr Phe Ser Thr Val Lys Asn Gly Glu Phe Ile Pro Gly Glu Val
            515                 520                 525

Lys Val Tyr Glu Val Thr Asp Thr Asn Ala Met Val Asp Ser Phe Asn
        530                 535                 540

Pro Asp Leu Asn Ser Ser Asn Val Lys Asp Val Thr Ser Gln Phe Ala
545                 550                 555                 560
```

```
Pro Lys Val Ser Ala Asp Gly Thr Arg Val Asp Ile Asn Phe Ala Arg
            565                 570                 575

Ser Met Ala Asn Gly Lys Lys Tyr Ile Val Thr Gln Ala Val Arg Pro
        580                 585                 590

Thr Gly Thr Gly Asn Val Tyr Thr Glu Tyr Trp Leu Thr Arg Asp Gly
    595                 600                 605

Thr Thr Asn Thr Asn Asp Phe Tyr Arg Gly Thr Lys Ser Thr Thr Val
        610                 615                 620

Thr Tyr Leu Asn Gly Ser Ser Thr Ala Gln Gly Asp Asn Pro
625                 630                 635

<210> SEQ ID NO 5
<211> LENGTH: 993
<212> TYPE: DNA
<213> ORGANISM: Staphylococcus epidermidis

<400> SEQUENCE: 5
atgagaggat cgcatcacca tcaccatcac ggatccccta atagtggtaa aaatgtgaat      60
gataaagtta aaatcacaaa ccctacgctt tcacttaata gagtaataa tcacgctaat     120 aacgtaatat ggccaacaag taacgaacaa tttaatttaa agcaaattga attagat      180 gacagcataa agagggaga tactttttact attaagtatg gtcagtatat tagaccgggt    240
ggtttagaac ttcctgcaat aaaaactcaa ctacgtagta aggatggctc tattgtagct    300
aatggtgtat atgataaaac tacaaatacg acgacttata catttactaa ctatgttgat    360
caatatcaaa atattacagg tagttttgat ttaattgcga cgcctaagag ggaaacagca    420
attaaggata tcagaatta tcctatggaa gtgacgattg ctaacgaagt agtcaaaaaa     480
gacttcattg tggattatgg taataaaaag gacaatacaa ctacagcagc ggtagcaaat    540
gtggataatg taaataataa acataacgaa gttgtttatc taaaccaaaa taaccaaaac    600
cctaaatatg ctaaatattt ctcaacagta aaaaatggtg aatttatacc aggtgaagtg    660
aaagtttacg aagtgacgga taccaatgcg atggtagata gcttcaatcc tgatttaaat    720
agttctaatg taaagatgt gacaagtcaa tttgcaccta agtaagtgc agatggtact     780 agagttgata tcaattttgc tagaagtatg gcaaatggta aaagtatat tgtaactcaa    840 gcagtgagac caacgggaac tggaaatgtt tataccgaat attggttaac aagagatggt    900
actaccaata caaatgattt ttaccgtgga acgaagtcta caacggtgac ttatctcaat    960
ggttcttcaa cagcacaggg ggataatcct tga                                 993

<210> SEQ ID NO 6
<211> LENGTH: 330
<212> TYPE: PRT
<213> ORGANISM: Staphylococcus epidermidis

<400> SEQUENCE: 6

Met Arg Gly Ser His His His His His His Gly Ser Pro Asn Ser Gly
1               5                   10                  15

Lys Asn Val Asn Asp Lys Val Lys Ile Thr Asn Pro Thr Leu Ser Leu
            20                  25                  30

Asn Lys Ser Asn Asn His Ala Asn Asn Val Ile Trp Pro Thr Ser Asn
        35                  40                  45

Glu Gln Phe Asn Leu Lys Ala Asn Tyr Glu Leu Asp Asp Ser Ile Lys
    50                  55                  60

Glu Gly Asp Thr Phe Thr Ile Lys Tyr Gly Gln Tyr Ile Arg Pro Gly
65                  70                  75                  80
```

```
Gly Leu Glu Leu Pro Ala Ile Lys Thr Gln Leu Arg Ser Lys Asp Gly
                85                  90                  95

Ser Ile Val Ala Asn Gly Val Tyr Asp Lys Thr Thr Asn Thr Thr Thr
            100                 105                 110

Tyr Thr Phe Thr Asn Tyr Val Asp Gln Tyr Gln Asn Ile Thr Gly Ser
        115                 120                 125

Phe Asp Leu Ile Ala Thr Pro Lys Arg Glu Thr Ala Ile Lys Asp Asn
130                 135                 140

Gln Asn Tyr Pro Met Glu Val Thr Ile Ala Asn Glu Val Val Lys Lys
145                 150                 155                 160

Asp Phe Ile Val Asp Tyr Gly Asn Lys Lys Asp Asn Thr Thr Thr Ala
                165                 170                 175

Ala Val Ala Asn Val Asp Asn Val Asn Asn Lys His Asn Glu Val Val
            180                 185                 190

Tyr Leu Asn Gln Asn Asn Gln Asn Pro Lys Tyr Ala Lys Tyr Phe Ser
        195                 200                 205

Thr Val Lys Asn Gly Glu Phe Ile Pro Gly Glu Val Lys Val Tyr Glu
    210                 215                 220

Val Thr Asp Thr Asn Ala Met Val Asp Ser Phe Asn Pro Asp Leu Asn
225                 230                 235                 240

Ser Ser Asn Val Lys Asp Val Thr Ser Gln Phe Ala Pro Lys Val Ser
                245                 250                 255

Ala Asp Gly Thr Arg Val Asp Ile Asn Phe Ala Arg Ser Met Ala Asn
            260                 265                 270

Gly Lys Lys Tyr Ile Val Thr Gln Ala Val Arg Pro Thr Gly Thr Gly
        275                 280                 285

Asn Val Tyr Thr Glu Tyr Trp Leu Thr Arg Asp Gly Thr Thr Asn Thr
    290                 295                 300

Asn Asp Phe Tyr Arg Gly Thr Lys Ser Thr Thr Val Thr Tyr Leu Asn
305                 310                 315                 320

Gly Ser Ser Thr Ala Gln Gly Asp Asn Pro
                325                 330

<210> SEQ ID NO 7
<211> LENGTH: 1434
<212> TYPE: DNA
<213> ORGANISM: Staphylococcus epidermidis

<400> SEQUENCE: 7
atgagaggat cgcatcacca tcaccatcac ggatccgctg aagacaatca attagaatca      60
gcttcaaaag aagaacagaa aggtagtcgt gataatgaaa actcaaaact taatcaagtc     120
gatttagaca acggatcaca tagttctgag aaaacaacaa atgtaaacaa tgcaactgaa     180
gtaaaaaaag ttgaagcacc aacgacaagt gacgtatcta agcctaaagc taatgaagca     240
gtagtgacga atgagtcaac taaaccaaaa acaacagaag caccaactgt taatgaggaa     300
tcaatagctg aaacacccaa aacctcaact acacaacaag attcgactga agaataat      360 ccatctttaa agataatttt aaattcatcc tcaacgacat ctaagaaag taaaacagac     420 gaacattcta ctaagcaagc tcaaatgtct actaataaat caaatttaga cacaaatgac     480
tctccaactc aaagtgagaa aacttcatca aagcaaata cgacagtac agataatcag     540 tcagcacctt ctaaacaatt agattcaaaa ccatcagaac aaaaagtata taaaacaaaa     600
tttaatgatg aacctactca agatgttgaa cacacgacaa ctaaattaaa acaccttct     660 gtttcaacag atagttcagt caatgataag caagattaca cacgaagtgc tgtagctagt     720
```

```
ttaggtgttg attctaatga aacagaagca attacaaatg cagttagaga caatttagat    780
ttaaaagctg catctagaga acaaatcaat gaagcaatca ttgctgaagc actaaaaaaa    840
gacttttcta accctgatta tggtgtcgat acgccattag ctctaaacag atctcaatca    900
aaaaattcac cacataagag tgcaagtcca cgcatgaatt taatgagttt agctgctgag    960
cctaatagtg gtaaaaatgt gaatgataaa gttaaaatca caaaccctac gctttcactt   1020
aataagagta ataatcacgc taataacgta atatggccaa caagtaacga acaatttaat   1080
ttaaaagcaa attatgaatt agatgacagc ataaagagg gagatacttt tactattaag    1140
tatggtcagt atattagacc gggtggttta gaacttcctg caataaaaac tcaactacgt   1200
agtaaggatg gctctattgt agctaatggt gtatatgata aaactacaaa tacgacgact   1260
tatacattta ctaactatgt tgatcaatat caaaatatta caggtagttt tgatttaatt   1320
gcgacgccta agagggaaac agcaattaag gataatcaga attatcctat ggaagtgacg   1380
attgctaacg aagtagtcaa aaaagacttc attgtggatt atggtaataa atga          1434
```

<210> SEQ ID NO 8
<211> LENGTH: 477
<212> TYPE: PRT
<213> ORGANISM: Staphylococcus epidermidis

<400> SEQUENCE: 8

```
Met Arg Gly Ser His His His His His His Gly Ser Ala Glu Asp Asn
 1               5                  10                  15

Gln Leu Glu Ser Ala Ser Lys Glu Glu Gln Lys Gly Ser Arg Asp Asn
            20                  25                  30

Glu Asn Ser Lys Leu Asn Gln Val Asp Leu Asp Asn Gly Ser His Ser
        35                  40                  45

Ser Glu Lys Thr Thr Asn Val Asn Asn Ala Thr Glu Val Lys Lys Val
    50                  55                  60

Glu Ala Pro Thr Thr Ser Asp Val Ser Lys Pro Lys Ala Asn Glu Ala
65                  70                  75                  80

Val Val Thr Asn Glu Ser Thr Lys Pro Lys Thr Thr Glu Ala Pro Thr
                85                  90                  95

Val Asn Glu Glu Ser Ile Ala Glu Thr Pro Lys Thr Ser Thr Thr Gln
            100                 105                 110

Gln Asp Ser Thr Glu Lys Asn Asn Pro Ser Leu Lys Asp Asn Leu Asn
        115                 120                 125

Ser Ser Ser Thr Ser Lys Gly Ser Lys Thr Asp Glu His Ser Thr
    130                 135                 140

Lys Gln Ala Gln Met Ser Thr Asn Lys Ser Asn Leu Asp Thr Asn Asp
145                 150                 155                 160

Ser Pro Thr Gln Ser Glu Lys Thr Ser Ser Gln Ala Asn Asn Asp Ser
                165                 170                 175

Thr Asp Asn Gln Ser Ala Pro Ser Lys Gln Leu Asp Ser Lys Pro Ser
            180                 185                 190

Glu Gln Lys Val Tyr Lys Thr Lys Phe Asn Asp Glu Pro Thr Gln Asp
        195                 200                 205

Val Glu His Thr Thr Thr Lys Leu Lys Thr Pro Ser Val Ser Thr Asp
    210                 215                 220

Ser Ser Val Asn Asp Lys Gln Asp Tyr Thr Arg Ser Ala Val Ala Ser
225                 230                 235                 240

Leu Gly Val Asp Ser Asn Glu Thr Glu Ala Ile Thr Asn Ala Val Arg
                245                 250                 255
```

```
Asp Asn Leu Asp Leu Lys Ala Ala Ser Arg Glu Gln Ile Asn Glu Ala
            260                 265                 270
Ile Ile Ala Glu Ala Leu Lys Lys Asp Phe Ser Asn Pro Asp Tyr Gly
                275                 280                 285
Val Asp Thr Pro Leu Ala Leu Asn Arg Ser Gln Ser Lys Asn Ser Pro
    290                 295                 300
His Lys Ser Ala Ser Pro Arg Met Asn Leu Met Ser Leu Ala Ala Glu
305                 310                 315                 320
Pro Asn Ser Gly Lys Asn Val Asn Asp Lys Val Lys Ile Thr Asn Pro
                325                 330                 335
Thr Leu Ser Leu Asn Lys Ser Asn His Ala Asn Asn Val Ile Trp
                340                 345                 350
Pro Thr Ser Asn Glu Gln Phe Asn Leu Lys Ala Asn Tyr Glu Leu Asp
                355                 360                 365
Asp Ser Ile Lys Glu Gly Asp Thr Phe Thr Ile Lys Tyr Gly Gln Tyr
    370                 375                 380
Ile Arg Pro Gly Gly Leu Glu Leu Pro Ala Ile Lys Thr Gln Leu Arg
385                 390                 395                 400
Ser Lys Asp Gly Ser Ile Val Ala Asn Gly Val Tyr Asp Lys Thr Thr
                405                 410                 415
Asn Thr Thr Thr Tyr Thr Phe Thr Asn Tyr Val Asp Gln Tyr Gln Asn
                420                 425                 430
Ile Thr Gly Ser Phe Asp Leu Ile Ala Thr Pro Lys Arg Glu Thr Ala
            435                 440                 445
Ile Lys Asp Asn Gln Asn Tyr Pro Met Glu Val Thr Ile Ala Asn Glu
    450                 455                 460
Val Val Lys Lys Asp Phe Ile Val Asp Tyr Gly Asn Lys
465                 470                 475

<210> SEQ ID NO 9
<211> LENGTH: 966
<212> TYPE: DNA
<213> ORGANISM: Staphylococcus epidermidis

<400> SEQUENCE: 9
atgagaggat cgcatcacca tcaccatcac ggatccgctg aagacaatca attagaatca      60
gcttcaaaag aagaacagaa aggtagtcgt gataatgaaa actcaaaact taatcaagtc     120
gatttagaca acggatcaca tagttctgag aaaacaacaa atgtaaacaa tgcaactgaa     180
gtaaaaaaag ttgaagcacc aacgacaagt gacgtatcta agcctaaagc taatgaagca     240
gtagtgacga atgagtcaac taaaccaaaa acaacagaag caccaactgt taatgaggaa     300
tcaatagctg aaacacccaa aacctcaact acacaacaag attcgactga agaagaataat     360 ccatctttaa aagataattt aaattcatcc tcaacgacat ctaaagaaag taaaacagac     420
gaacattcta ctaagcaagc tcaaatgtct actaataaat caaatttaga cacaaatgac     480
tctccaactc aaagtgagaa aacttcatca caagcaaata cgacagtac agataatcag     540 tcagcaccctt ctaaacaatt agattcaaaa ccatcagaac aaaaagtata taaaacaaaa     600
tttaatgatg aacctactca agatgttgaa cacacgacaa ctaaattaaa acaccttct     660 gtttcaacag atagttcagt caatgataag caagattaca cacgaagtgc tgtagctagt     720
ttaggtgttg attctaatga aacagaagca attacaaatg cagttagaga caatttagat     780
ttaaaagctg catctagaga acaaatcaat gaagcaatca ttgctgaagc actaaaaaaa     840
gacttttcta accctgatta tggtgtcgat acgccattag ctctaaacag atctcaatca     900
```

```
aaaaattcac cacataagag tgcaagtcca cgcatgaatt taatgagttt agctgctgag    960
ccttga                                                              966
```

```
<210> SEQ ID NO 10
<211> LENGTH: 321
<212> TYPE: PRT
<213> ORGANISM: Staphylococcus epidermidis

<400> SEQUENCE: 10
```

Met Arg Gly Ser His His His His His His Gly Ser Ala Glu Asp Asn
1               5                   10                  15

Gln Leu Glu Ser Ala Ser Lys Glu Gln Lys Gly Ser Arg Asp Asn
            20                  25                  30

Glu Asn Ser Lys Leu Asn Gln Val Asp Leu Asp Asn Gly Ser His Ser
                35                  40                  45

Ser Glu Lys Thr Thr Asn Val Asn Asn Ala Thr Glu Val Lys Lys Val
    50                  55                  60

Glu Ala Pro Thr Thr Ser Asp Val Ser Lys Pro Lys Ala Asn Glu Ala
65                  70                  75                  80

Val Val Thr Asn Glu Ser Thr Lys Pro Lys Thr Thr Glu Ala Pro Thr
                85                  90                  95

Val Asn Glu Glu Ser Ile Ala Glu Thr Pro Lys Thr Ser Thr Thr Gln
            100                 105                 110

Gln Asp Ser Thr Glu Lys Asn Asn Pro Ser Leu Lys Asp Asn Leu Asn
        115                 120                 125

Ser Ser Ser Thr Thr Ser Lys Glu Ser Lys Thr Asp Glu His Ser Thr
130                 135                 140

Lys Gln Ala Gln Met Ser Thr Asn Lys Ser Asn Leu Asp Thr Asn Asp
145                 150                 155                 160

Ser Pro Thr Gln Ser Glu Lys Thr Ser Ser Gln Ala Asn Asn Asp Ser
                165                 170                 175

Thr Asp Asn Gln Ser Ala Pro Ser Lys Gln Leu Asp Ser Lys Pro Ser
            180                 185                 190

Glu Gln Lys Val Tyr Lys Thr Lys Phe Asn Asp Glu Pro Thr Gln Asp
        195                 200                 205

Val Glu His Thr Thr Thr Lys Leu Lys Thr Pro Ser Val Ser Thr Asp
    210                 215                 220

Ser Ser Val Asn Asp Lys Gln Asp Tyr Thr Arg Ser Ala Val Ala Ser
225                 230                 235                 240

Leu Gly Val Asp Ser Asn Glu Thr Glu Ala Ile Thr Asn Ala Val Arg
                245                 250                 255

Asp Asn Leu Asp Leu Lys Ala Ala Ser Arg Glu Gln Ile Asn Glu Ala
            260                 265                 270

Ile Ile Ala Glu Ala Leu Lys Lys Asp Phe Ser Asn Pro Asp Tyr Gly
        275                 280                 285

Val Asp Thr Pro Leu Ala Leu Asn Arg Ser Gln Ser Lys Asn Ser Pro
    290                 295                 300

His Lys Ser Ala Ser Pro Arg Met Asn Leu Met Ser Leu Ala Ala Glu
305                 310                 315                 320

Pro

```
<210> SEQ ID NO 11
<211> LENGTH: 510
<212> TYPE: DNA
<213> ORGANISM: Staphylococcus epidermidis
```

-continued

<400> SEQUENCE: 11

```
atgagaggat cgcatcacca tcaccatcac ggatcccta atagtggtaa aaatgtgaat    60
gataaagtta aaatcacaaa ccctacgctt tcacttaata agagtaataa tcacgctaat   120
aacgtaatat ggccaacaag taacgaacaa tttaatttaa agcaaatta tgaattagat    180
gacagcataa aagagggaga tacttttact attaagtatg gtcagtatat tagaccgggt   240
ggtttagaac ttcctgcaat aaaaactcaa ctacgtagta aggatggctc tattgtagct   300
aatggtgtat atgataaaac tacaaatacg acgacttata catttactaa ctatgttgat   360
caatatcaaa atattacagg tagttttgat ttaattgcga cgcctaagag ggaaacagca   420
attaaggata atcagaatta tcctatggaa gtgacgattg ctaacgaagt agtcaaaaaa   480
gacttcattg tggattatgg taataaatga                                    510
```

<210> SEQ ID NO 12
<211> LENGTH: 169
<212> TYPE: PRT
<213> ORGANISM: Staphylococcus epidermidis

<400> SEQUENCE: 12

```
Met Arg Gly Ser His His His His His His Gly Ser Pro Asn Ser Gly
1               5                   10                  15
Lys Asn Val Asn Asp Lys Val Lys Ile Thr Asn Pro Thr Leu Ser Leu
            20                  25                  30
Asn Lys Ser Asn Asn His Ala Asn Asn Val Ile Trp Pro Thr Ser Asn
        35                  40                  45
Glu Gln Phe Asn Leu Lys Ala Asn Tyr Glu Leu Asp Asp Ser Ile Lys
    50                  55                  60
Glu Gly Asp Thr Phe Thr Ile Lys Tyr Gly Gln Tyr Ile Arg Pro Gly
65                  70                  75                  80
Gly Leu Glu Leu Pro Ala Ile Lys Thr Gln Leu Arg Ser Lys Asp Gly
                85                  90                  95
Ser Ile Val Ala Asn Gly Val Tyr Asp Lys Thr Thr Asn Thr Thr Thr
            100                 105                 110
Tyr Thr Phe Thr Asn Tyr Val Asp Gln Tyr Gln Asn Ile Thr Gly Ser
        115                 120                 125
Phe Asp Leu Ile Ala Thr Pro Lys Arg Glu Thr Ala Ile Lys Asp Asn
    130                 135                 140
Gln Asn Tyr Pro Met Glu Val Thr Ile Ala Asn Glu Val Val Lys Lys
145                 150                 155                 160
Asp Phe Ile Val Asp Tyr Gly Asn Lys
                165
```

<210> SEQ ID NO 13
<211> LENGTH: 525
<212> TYPE: DNA
<213> ORGANISM: Staphylococcus epidermidis

<400> SEQUENCE: 13

```
atgagaggat cgcatcacca tcaccatcac ggatccaaaa aggacaatac aactacagca    60
gcggtagcaa atgtggataa tgtaaataat aaacataacg aagttgttta tctaaaccaa   120
aataaccaaa accctaaata tgctaaatat ttctcaacag taaaaaatgg tgaatttata   180
ccaggtgaag tgaaagttta cgaagtgacg gataccaatg cgatggtaga tagcttcaat   240
cctgatttaa atagttctaa tgtaaaagat gtgacaagtc aatttgcacc taaagtaagt   300
gcagatggta ctagagttga tatcaatttt gctagaagta tggcaaatgg taaaaagtat   360
```

```
attgtaactc aagcagtgag accaacggga actggaaatg tttataccga atattggtta      420
acaagagatg gtactaccaa tacaaatgat ttttaccgtg aacgaagtc tacaacggtg       480 acttatctca atggttcttc aacagcacag ggggataatc cttga                     525
```

<210> SEQ ID NO 14
<211> LENGTH: 174
<212> TYPE: PRT
<213> ORGANISM: Staphylococcus epidermidis

<400> SEQUENCE: 14

```
Met Arg Gly Ser His His His His His His Gly Ser Lys Lys Asp Asn
1               5                   10                  15

Thr Thr Thr Ala Ala Val Ala Asn Val Asp Asn Val Asn Asn Lys His
            20                  25                  30

Asn Glu Val Val Tyr Leu Asn Gln Asn Asn Gln Asn Pro Lys Tyr Ala
        35                  40                  45

Lys Tyr Phe Ser Thr Val Lys Asn Gly Glu Phe Ile Pro Gly Glu Val
    50                  55                  60

Lys Val Tyr Glu Val Thr Asp Thr Asn Ala Met Val Asp Ser Phe Asn
65                  70                  75                  80

Pro Asp Leu Asn Ser Ser Asn Val Lys Asp Val Thr Ser Gln Phe Ala
                85                  90                  95

Pro Lys Val Ser Ala Asp Gly Thr Arg Val Asp Ile Asn Phe Ala Arg
            100                 105                 110

Ser Met Ala Asn Gly Lys Lys Tyr Ile Val Thr Gln Ala Val Arg Pro
        115                 120                 125

Thr Gly Thr Gly Asn Val Tyr Thr Glu Tyr Trp Leu Thr Arg Asp Gly
    130                 135                 140

Thr Thr Asn Thr Asn Asp Phe Tyr Arg Gly Thr Lys Ser Thr Thr Val
145                 150                 155                 160

Thr Tyr Leu Asn Gly Ser Ser Thr Ala Gln Gly Asp Asn Pro
                165                 170
```

<210> SEQ ID NO 15
<211> LENGTH: 324
<212> TYPE: DNA
<213> ORGANISM: Staphylococcus epidermidis

<400> SEQUENCE: 15

```
gacattgtga tgacccagtc tcacaaattc atgtccacat cagtaggaga cagggtcatc      60
atcacctgca aggccagtca ggatgtgaat actgctctag cctggtatca gcagaaacca     120
ggacaatctc ctaaactact gatttactcg gcatcctacc ggtatactgg agtccctgat     180
cgcttcactg gcagtggatc tgggacggat ttcactttca ccatcagcag tgtgcaggct     240
gaagacctgg cagtttatta ctgtcagcaa cattatagta cccctccgta cacgttcgga     300
gggggaccaa gctggagat aaaa                                             324
```

<210> SEQ ID NO 16
<211> LENGTH: 108
<212> TYPE: PRT
<213> ORGANISM: Staphylococcus epidermidis

<400> SEQUENCE: 16

```
Asp Ile Val Met Thr Gln Ser His Lys Phe Met Ser Thr Ser Val Gly
1               5                   10                  15

Asp Arg Val Ile Ile Thr Cys Lys Ala Ser Gln Asp Val Asn Thr Ala
            20                  25                  30
```

```
Leu Ala Trp Tyr Gln Gln Lys Pro Gly Gln Ser Pro Lys Leu Leu Ile
         35                  40                  45

Tyr Ser Ala Ser Tyr Arg Tyr Thr Gly Val Pro Asp Arg Phe Thr Gly
     50                  55                  60

Ser Gly Ser Gly Thr Asp Phe Thr Phe Thr Ile Ser Ser Val Gln Ala
65                  70                  75                  80

Glu Asp Leu Ala Val Tyr Tyr Cys Gln Gln His Tyr Ser Thr Pro Pro
                 85                  90                  95

Tyr Thr Phe Gly Gly Gly Thr Lys Leu Glu Ile Lys
            100                 105
```

<210> SEQ ID NO 17
<211> LENGTH: 351
<212> TYPE: DNA
<213> ORGANISM: Staphylococcus epidermidis

<400> SEQUENCE: 17

| | | | | | |
|---|---|---|---|---|---|
| gaggttcagc | tgcagcagtc | tggggcagag | cttgtgaagc | caggggcctc | agtcaagttg | 60 |
| tcctgcacag | cttctggctt | caacattaaa | gacacctata | tacactgggt | gaagcagagg | 120 |
| cctgaacagg | gcctggagtg | gattggaagg | attgatcctg | cgaatggtaa | tactcattat | 180 |
| gactcacagt | tccagggcaa | ggccactata | acagcagaca | catcctccaa | cacagcctac | 240 |
| ctgcagctca | gcagcctgac | atctgacgac | actgccgtct | attactgtac | tagacgtgtg | 300 |
| ggctatgcta | tggactactg | gggtcaagga | acctcagtca | ccgtctcctc | a | 351 |

<210> SEQ ID NO 18
<211> LENGTH: 117
<212> TYPE: PRT
<213> ORGANISM: Staphylococcus epidermidis

<400> SEQUENCE: 18

```
Glu Val Gln Leu Gln Gln Ser Gly Ala Glu Leu Val Lys Pro Gly Ala
1               5                   10                  15

Ser Val Lys Leu Ser Cys Thr Ala Ser Gly Phe Asn Ile Lys Asp Thr
            20                  25                  30

Tyr Ile His Trp Val Lys Gln Arg Pro Glu Gln Gly Leu Glu Trp Ile
         35                  40                  45

Gly Arg Ile Asp Pro Ala Asn Gly Asn Thr His Tyr Asp Ser Gln Phe
     50                  55                  60

Gln Gly Lys Ala Thr Ile Thr Ala Asp Thr Ser Ser Asn Thr Ala Tyr
65                  70                  75                  80

Leu Gln Leu Ser Ser Leu Thr Ser Asp Asp Thr Ala Val Tyr Tyr Cys
                 85                  90                  95

Thr Arg Arg Val Gly Tyr Ala Met Asp Tyr Trp Gly Gln Gly Thr Ser
            100                 105                 110

Val Thr Val Ser Ser
        115
```

<210> SEQ ID NO 19
<211> LENGTH: 318
<212> TYPE: DNA
<213> ORGANISM: Staphylococcus epidermidis

<400> SEQUENCE: 19

| | | | | | |
|---|---|---|---|---|---|
| caaattgttc | tcacccagtc | tccagcaatc | atgtctgcat | ctccagggga | gaaggtcacc | 60 |
| atgacctgca | gtgccagctc | aagtgtaagt | tacatgtact | ggtaccaaca | gaaaccagga | 120 |
| tcctccccca | gagtcctgat | ttatgacaca | tccaacctgg | cttctggagt | ccctgttcgc | 180 |

```
ttcagtggca gtgggtctgg gacctcttac tctctcacaa tcagccgaat ggaggctgaa    240
gatgctgcca cttattactg ccagcagtgg aatggttatc cacccacgtt cggtgctggg    300
accaagctgg aggtgaaa                                                  318
```

```
<210> SEQ ID NO 20
<211> LENGTH: 106
<212> TYPE: PRT
<213> ORGANISM: Staphylococcus epidermidis

<400> SEQUENCE: 20
```

Gln Ile Val Leu Thr Gln Ser Pro Ala Ile Met Ser Ala Ser Pro Gly
1               5                  10                  15

Glu Lys Val Thr Met Thr Cys Ser Ala Ser Ser Ser Val Ser Tyr Met
            20                  25                  30

Tyr Trp Tyr Gln Gln Lys Pro Gly Ser Ser Pro Arg Val Leu Ile Tyr
        35                  40                  45

Asp Thr Ser Asn Leu Ala Ser Gly Val Pro Val Arg Phe Ser Gly Ser
    50                  55                  60

Gly Ser Gly Thr Ser Tyr Ser Leu Thr Ile Ser Arg Met Glu Ala Glu
65                  70                  75                  80

Asp Ala Ala Thr Tyr Tyr Cys Gln Gln Trp Asn Gly Tyr Pro Pro Thr
                85                  90                  95

Phe Gly Ala Gly Thr Lys Leu Glu Val Lys
            100                 105

```
<210> SEQ ID NO 21
<211> LENGTH: 369
<212> TYPE: DNA
<213> ORGANISM: Staphylococcus epidermidis

<400> SEQUENCE: 21
```

```
caggttactc tgagagagtc tggccctggg atattgcagc cctcccagac cctcagtctg     60
acttgttctt tctctgggtt ttcactgaac acttctggta tgggtgtgac ctggattcgt    120
cagccttctg gaaagggtct ggagtggctg gcaaacattt actgggatga tgacaagcgc    180
tataacccat ccctgaagag ccggctcaca atctccaagg ctaactccag aaaccaggta    240
ttcctcaaga tcaccagtgt ggacactgca gatactgcca catactactg tactcgcccc    300
aattacctcg gtactgtcta ctggtacttt gatgtctggg gcgcagggac catggtcacc    360
gtctcctca                                                            369
```

```
<210> SEQ ID NO 22
<211> LENGTH: 123
<212> TYPE: PRT
<213> ORGANISM: Staphylococcus epidermidis

<400> SEQUENCE: 22
```

Gln Val Thr Leu Arg Glu Ser Gly Pro Gly Ile Leu Gln Pro Ser Gln
1               5                  10                  15

Thr Leu Ser Leu Thr Cys Ser Phe Ser Gly Phe Ser Leu Asn Thr Ser
            20                  25                  30

Gly Met Gly Val Thr Trp Ile Arg Gln Pro Ser Gly Lys Gly Leu Glu
        35                  40                  45

Trp Leu Ala Asn Ile Tyr Trp Asp Asp Asp Lys Arg Tyr Asn Pro Ser
    50                  55                  60

Leu Lys Ser Arg Leu Thr Ile Ser Lys Ala Asn Ser Arg Asn Gln Val
65                  70                  75                  80

```
Phe Leu Lys Ile Thr Ser Val Asp Thr Ala Asp Thr Ala Thr Tyr Tyr
                85                  90                  95
Cys Thr Arg Pro Asn Tyr Leu Gly Thr Val Tyr Trp Tyr Phe Asp Val
            100                 105                 110
Trp Gly Ala Gly Thr Met Val Thr Val Ser Ser
        115                 120
```

<210> SEQ ID NO 23
<211> LENGTH: 318
<212> TYPE: DNA
<213> ORGANISM: Staphylococcus epidermidis

<400> SEQUENCE: 23

```
caaattgttc tcacccagtc tccagcaatc atgtctgcat ctccagggga ggagggcacc    60
atgacctgca gtgccagctc aagtgtaagg tacatgtact ggtaccggca gaagccagga   120
tcctccccca gactcttgat ttatgacaca tccaacctgg cttctggagt ccctgttcgc   180
ttcagtggca gtgggtctgg gacctcttac tctctcacaa tcagccgaat ggaggctgaa   240
gatgctgcca cttattactg ccagcagtgg agtagttacc cacccacgtt cggagggggg   300
accaagctgg aaatgaaa                                                  318
```

<210> SEQ ID NO 24
<211> LENGTH: 106
<212> TYPE: PRT
<213> ORGANISM: Staphylococcus epidermidis

<400> SEQUENCE: 24

```
Gln Ile Val Leu Thr Gln Ser Pro Ala Ile Met Ser Ala Ser Pro Gly
1               5                   10                  15
Glu Glu Gly Thr Met Thr Cys Ser Ala Ser Ser Ser Val Arg Tyr Met
            20                  25                  30
Tyr Trp Tyr Arg Gln Lys Pro Gly Ser Ser Pro Arg Leu Leu Ile Tyr
        35                  40                  45
Asp Thr Ser Asn Leu Ala Ser Gly Val Pro Val Arg Phe Ser Gly Ser
    50                  55                  60
Gly Ser Gly Thr Ser Tyr Ser Leu Thr Ile Ser Arg Met Glu Ala Glu
65                  70                  75                  80
Asp Ala Ala Thr Tyr Tyr Cys Gln Gln Trp Ser Ser Tyr Pro Pro Thr
                85                  90                  95
Phe Gly Gly Gly Thr Lys Leu Glu Met Lys
            100                 105
```

<210> SEQ ID NO 25
<211> LENGTH: 354
<212> TYPE: DNA
<213> ORGANISM: Staphylococcus epidermidis

<400> SEQUENCE: 25

```
gaagtgcagt tggtggagtc tgggggaggc ttagtgaagc ctggagggtc cctgaaactc    60
tcctgtgcag cctctggatt cgctttcagt agctatgaca tgtcttgggt tcgccagact   120
ccggagaaga ggctggagtg gtcgcctac attagtagtg gtggtggtat cacctactat   180
ccagacactg tgaagggccg attcaccatc tccagagaca atgccaagaa cacccctgtac   240
gtgcaaatga gcagtctgaa gtctgaggac acagccattt attattgtac aagacacgat   300
agggactcct ggtttgctta ttggggccaa gggactctgg tcactgtctc tgca          354
```

```
<210> SEQ ID NO 26
<211> LENGTH: 118
<212> TYPE: PRT
<213> ORGANISM: Staphylococcus epidermidis

<400> SEQUENCE: 26

Glu Val Gln Leu Val Glu Ser Gly Gly Gly Leu Val Lys Pro Gly Gly
1               5                   10                  15

Ser Leu Lys Leu Ser Cys Ala Ala Ser Gly Phe Ala Phe Ser Ser Tyr
            20                  25                  30

Asp Met Ser Trp Val Arg Gln Thr Pro Glu Lys Arg Leu Glu Trp Val
        35                  40                  45

Ala Tyr Ile Ser Ser Gly Gly Gly Ile Thr Tyr Tyr Pro Asp Thr Val
    50                  55                  60

Lys Gly Arg Phe Thr Ile Ser Arg Asp Asn Ala Lys Asn Thr Leu Tyr
65                  70                  75                  80

Val Gln Met Ser Ser Leu Lys Ser Glu Asp Thr Ala Ile Tyr Tyr Cys
                85                  90                  95

Thr Arg His Asp Arg Asp Ser Trp Phe Ala Tyr Trp Gly Gln Gly Thr
            100                 105                 110

Leu Val Thr Val Ser Ala
        115

<210> SEQ ID NO 27
<211> LENGTH: 108
<212> TYPE: PRT
<213> ORGANISM: Staphylococcus epidermidis

<400> SEQUENCE: 27

Asp Ile Val Met Thr Gln Ser Gln Lys Phe Met Ser Thr Ser Val Gly
1               5                   10                  15

Asp Arg Val Thr Ile Thr Cys Lys Ala Ser Gln Asp Val Asn Thr Ala
            20                  25                  30

Leu Ala Trp Tyr Gln Gln Lys Pro Gly Gln Ser Pro Lys Leu Leu Ile
        35                  40                  45

Tyr Ser Ala Ser Tyr Arg Tyr Thr Gly Val Pro Ser Arg Phe Ser Gly
    50                  55                  60

Ser Gly Ser Gly Thr Asp Phe Thr Phe Thr Ile Ser Ser Val Gln Ala
65                  70                  75                  80

Glu Asp Leu Ala Val Tyr Tyr Cys Gln Gln His Tyr Ser Thr Pro Pro
                85                  90                  95

Tyr Thr Phe Gly Gly Gly Thr Lys Leu Glu Ile Lys
            100                 105

<210> SEQ ID NO 28
<211> LENGTH: 117
<212> TYPE: PRT
<213> ORGANISM: Staphylococcus epidermidis

<400> SEQUENCE: 28

Gln Val Gln Leu Val Gln Ser Gly Ala Glu Val Val Lys Pro Gly Ala
1               5                   10                  15

Ser Val Lys Leu Ser Cys Lys Ala Ser Gly Phe Asn Ile Lys Asp Thr
            20                  25                  30

Tyr Ile His Trp Val Lys Gln Arg Pro Gly Gln Gly Leu Glu Trp Ile
        35                  40                  45

Gly Arg Ile Asp Pro Ala Asn Gly Asn Thr His Tyr Asp Ser Gln Phe
    50                  55                  60
```

```
Gln Gly Lys Ala Thr Ile Thr Ala Asp Thr Ser Ser Thr Ala Tyr
 65                  70                  75                  80

Leu Gln Leu Ser Ser Leu Arg Ser Glu Asp Thr Ala Val Tyr Tyr Cys
                 85                  90                  95

Thr Arg Arg Val Gly Tyr Ala Met Asp Tyr Trp Gly Gln Gly Thr Thr
            100                 105                 110

Val Thr Val Ser Ser
            115

<210> SEQ ID NO 29
<211> LENGTH: 106
<212> TYPE: PRT
<213> ORGANISM: Staphylococcus epidermidis

<400> SEQUENCE: 29

Glu Ile Val Leu Thr Gln Ser Pro Ala Thr Met Ser Ala Ser Pro Gly
  1               5                  10                  15

Glu Arg Val Thr Met Ser Cys Ser Ala Ser Ser Val Ser Tyr Met
                 20                  25                  30

Tyr Trp Tyr Gln Gln Lys Pro Gly Gln Ser Pro Arg Val Leu Ile Tyr
                 35                  40                  45

Asp Thr Ser Asn Leu Ala Ser Gly Val Pro Ser Arg Phe Ser Gly Ser
             50                  55                  60

Gly Ser Gly Thr Ser Tyr Ser Leu Thr Ile Ser Ser Met Glu Pro Glu
 65                  70                  75                  80

Asp Ala Ala Thr Tyr Tyr Cys Gln Gln Trp Asn Gly Tyr Pro Pro Thr
                 85                  90                  95

Phe Gly Gly Gly Thr Lys Leu Glu Val Lys
            100                 105

<210> SEQ ID NO 30
<211> LENGTH: 123
<212> TYPE: PRT
<213> ORGANISM: Staphylococcus epidermidis

<400> SEQUENCE: 30

Gln Val Thr Leu Arg Glu Ser Gly Pro Gly Ile Leu Lys Pro Ser Gln
  1               5                  10                  15

Thr Leu Ser Leu Thr Cys Thr Phe Ser Gly Phe Ser Leu Asn Thr Ser
                 20                  25                  30

Gly Met Gly Val Thr Trp Ile Arg Gln Pro Ser Gly Lys Gly Leu Glu
             35                  40                  45

Trp Leu Ala Asn Ile Tyr Trp Asp Asp Asp Lys Arg Tyr Asn Pro Ser
 50                  55                  60

Leu Lys Ser Arg Leu Thr Ile Ser Lys Ala Asn Ser Arg Asn Gln Val
 65                  70                  75                  80

Phe Leu Lys Ile Thr Ser Val Asp Pro Val Asp Thr Ala Thr Tyr Tyr
                 85                  90                  95

Cys Thr Arg Pro Asn Tyr Leu Gly Thr Val Tyr Trp Tyr Phe Asp Val
            100                 105                 110

Trp Gly Gln Gly Thr Met Val Thr Val Ser Ser
            115                 120

<210> SEQ ID NO 31
<211> LENGTH: 106
<212> TYPE: PRT
<213> ORGANISM: Staphylococcus epidermidis
```

<400> SEQUENCE: 31

Glu Ile Val Leu Thr Gln Ser Pro Gly Thr Met Ser Ala Ser Pro Gly
1               5                   10                  15

Glu Arg Gly Thr Met Ser Cys Ser Ala Ser Ser Val Arg Tyr Met
            20                  25                  30

Tyr Trp Tyr Arg Gln Lys Pro Gly Gln Ser Pro Arg Leu Leu Ile Tyr
        35                  40                  45

Asp Thr Ser Asn Leu Ala Ser Gly Val Pro Ala Arg Phe Ser Gly Ser
    50                  55                  60

Gly Ser Gly Thr Ser Tyr Ser Leu Thr Ile Ser Arg Met Glu Ala Glu
65                  70                  75                  80

Asp Ala Ala Thr Tyr Tyr Cys Gln Gln Trp Ser Tyr Pro Pro Thr
                85                  90                  95

Phe Gly Gly Gly Thr Lys Leu Glu Met Lys
            100                 105

<210> SEQ ID NO 32
<211> LENGTH: 118
<212> TYPE: PRT
<213> ORGANISM: Staphylococcus epidermidis

<400> SEQUENCE: 32

Glu Val Gln Leu Val Glu Ser Gly Gly Gly Leu Val Gln Pro Gly Gly
1               5                   10                  15

Ser Leu Lys Leu Ser Cys Ala Ala Ser Gly Phe Ala Phe Ser Ser Tyr
            20                  25                  30

Asp Met Ser Trp Val Arg Gln Thr Pro Glu Lys Arg Leu Glu Trp Val
        35                  40                  45

Ala Tyr Ile Ser Ser Gly Gly Gly Ile Thr Tyr Tyr Pro Asp Thr Val
    50                  55                  60

Lys Gly Arg Phe Thr Ile Ser Arg Asp Asn Ser Lys Asn Thr Leu Tyr
65                  70                  75                  80

Val Gln Met Ser Ser Leu Arg Ala Glu Asp Thr Ala Val Tyr Tyr Cys
                85                  90                  95

Thr Arg His Asp Arg Asp Ser Trp Phe Ala Tyr Trp Gly Gln Gly Thr
            100                 105                 110

Leu Val Thr Val Ser Ser
        115

<210> SEQ ID NO 33
<211> LENGTH: 369
<212> TYPE: DNA
<213> ORGANISM: Staphylococcus epidermidis

<400> SEQUENCE: 33
caggttactc tgagagagtc tggccctggg atattgaagc cctcccagac cctcagtctg    60
acttgtacct tctctgggtt ttcactgagc acttctggta tgggtgtgac ctggattcgc   120
cagccttctg gaaagggtct ggagtggctg gcaaacattt actgggatga tgacaagcgc   180
tataacccat ccctgaagag ccggctcaca atctccaagg ctaactccag aaaccaggtg   240
ttcctcaaga tcaccagtgt ggaccccgtg gatactgcca catactactg tactcgcccc   300
aattacctgg gtactgtgta ctggtacttt gatgtctggg gccaggggac catggtgacc   360
gtgtcctca                                                           369

```
<210> SEQ ID NO 34
<211> LENGTH: 123
<212> TYPE: PRT
<213> ORGANISM: Staphylococcus epidermidis

<400> SEQUENCE: 34

Gln Val Thr Leu Arg Glu Ser Gly Pro Gly Ile Leu Lys Pro Ser Gln
1               5                   10                  15

Thr Leu Ser Leu Thr Cys Thr Phe Ser Gly Phe Ser Leu Ser Thr Ser
            20                  25                  30

Gly Met Gly Val Thr Trp Ile Arg Gln Pro Ser Gly Lys Gly Leu Glu
            35                  40                  45

Trp Leu Ala Asn Ile Tyr Trp Asp Asp Asp Lys Arg Tyr Asn Pro Ser
    50                  55                  60

Leu Lys Ser Arg Leu Thr Ile Ser Lys Ala Asn Ser Arg Asn Gln Val
65                  70                  75                  80

Phe Leu Lys Ile Thr Ser Val Asp Pro Val Asp Thr Ala Thr Tyr Tyr
                85                  90                  95

Cys Thr Arg Pro Asn Tyr Leu Gly Thr Val Tyr Trp Tyr Phe Asp Val
            100                 105                 110

Trp Gly Gln Gly Thr Met Val Thr Val Ser Ser
            115                 120
```

MONOCLONAL ANTIBODIES RECOGNIZING A COAGULASE-NEGATIVE *STAPHYLOCOCCAL* PROTEIN

CROSS REFERENCE TO RELATED APPLICATIONS

The present application claims the benefit of U.S. provisional application Ser. No. 60/690,940 filed Jun. 16, 2005, incorporated herein by reference.

FIELD OF THE INVENTION

The present invention relates to the fields of microbiology, molecular biology, and immunology and more particularly relates to newly identified monoclonal antibodies, the use of monoclonal antibodies, as well as the production of such monoclonal antibodies and recombinant host cells transformed with the DNA encoding monoclonal antibodies to prevent, treat, or diagnose coagulase-negative staphylococcal infections in man and animals. The invention includes murine, chimeric, humanized, and human monoclonal antibodies, as well as fragments, regions and derivatives thereof. The antibodies detailed in this invention specifically recognize SdrF, an extracellular matrix binding MSCRAMM® protein expressed by coagulase-negative staphylococci, particularly *S. epidermidis.*

BACKGROUND OF THE INVENTION

Coagulase-negative staphylococci, particularly *Staphylococcus epidermidis* is a generally avirulent commensal organism of the human skin, and is the principle etiologic agent of infections of peripheral and central venous catheters, prosthetic heart valves, artificial joints, and other prosthetic devices. *S. epidermidis* bacteremia has an attributable mortality rate of 10-34% and results in an excess hospital stay of 8 days, and costs an estimated $6,000.00 per case. Despite its importance as a nosocomial pathogen, relatively little is known about the pathogenesis of these infections or the virulence determinants of this organism. Initial localized infections of indwelling medical devices can lead to more serious invasive infections such as septicemia, osteomyelitis, and endocarditis. Vascular catheters are thought to become infected when microorganisms gain access to the device, and hence the blood stream, by migration from the skin surface down the transcutaneous portion of the catheter. In infections associated with medical devices, plastic and metal surfaces become coated with host plasma and matrix proteins such as fibrinogen, vitronectin and fibronectin shortly after implantation. The ability of coagulase-negative staphylococci to adhere to these proteins is of crucial importance for initiating infection. Bacterial or microorganism adherence is thought to be the first crucial step in the pathogenesis of a prosthetic device infection. A number of factors influence an organism's ability to adhere to prosthetic material. These include characteristics of the microorganism and the biomaterial, and the nature of the ambient milieu. The initial attraction between the organism and the host is influenced by nonspecific forces such as surface charge, polarity, Van der Waal forces and hydrophobic interactions. The critical stage of adherence involves specific interactions between MSCRAMM® proteins and immobilized host proteins. To date, investigation concerning the adherence of coagulase negative staphylococci to biomaterials has concerned itself primarily with the role of the extracellular polysaccharide or glycocalyx, also known as slime. Despite intensive study however, the proposed role of slime in the pathogenesis of disease or even its composition remain debated. Drewry. D. T., L Gailbraith. B. I. Wilkinson, and S. G. Wilkinson. 1990. *Staphylococcal Slime: A Cautionary Tale, I.* Clin. Microbiol 28; 1292-1296. Currently, extracellular slime is thought to play a role in the later stages of adherence and persistence of infection. It may serve as an ion exchange resin to optimize a local nutritional environment, prevent penetration of antibiotics into the macro-colony and protect bacteria from phagocytic host defense cells. Peters et al have shown by electron microscopy studies that extracellular polysaccharide appears in the later stages of attachment and is not present during the initial phase of adherence. Peters, O., R. Locci. and G. Pulverer. 1982. *Adherence and Growth of Coagulase-Negative Staphylococci on Surfaces in Intravenous Catheters. I. Infect Dis.* 65146: 479-482. Hogt et al demonstrated that removal of the extracellular slime layer by repeated washing does not diminish the ability of *S. epidermidis* to adhere to biomaterials. Hogt. A. H., I. Dankert, I. A. DeVries. and I. Feijen, 1983. *Adhesion of Coagulase-Negative Staphylococci to Bloinaterials. J. Gen. Microbial.* 129:2959-2968.

Thus study of exopolysaccharide has tended little to prevention of initial adherence by the bacteria. Several other studies have identified other potential adhesins of *S. epidermidis* including the polysaccharide adhesion (PS/A) observed by Tojo et al. Tojo, M., N. Yamashita, D. A. Goldmann. and G. B. Pier, 1988. *Isolation and Characterization of a Capsular Polysaccharide Adhesin* 10 *from Staphylococcus epidermidis. J. Infect. Dis.* 157:713-722. The slime associated antigen at (SAA) of Christensen et al. Christensen. G. D., Barker, L. P., Manhinnes, T. P., Baddour, L. M., Simpson. W. A. *Identification of an Antigenic Marker of Slime Production for Staphylococcus epidermidis. Infect Immun.* 1990; 58:2906-2911.

It has been demonstrated that PS/A is a complex mixture of monosaccharides and purified PS/A blocks adherence of PS/A producing strains of *S. epidermidis*. In an animal model of endocarditis antibodies directed against PS/A was protective. However it is not clear whether this protective effect was specific, related to anti-adhesive effects of the antibody or due to a more generalized increase in the efficiency of opsonophagocytosis of blood borne bacteria. It has been hypothesized that each functions in different stages of the adherence process with one or more of these adhesins responsible for initial attraction while other are needed for aggregation in the macro-colonies. Despite all of these studies, factors involved in the initial adherence of *S. epidermidis* to biomaterials remain largely unknown and equally unknown is a practical method for preventing the first stage of infection, adherence.

One particular area where improved treatment regimens is needed is the prevention/treatment of coagulase negative staphylococcal infections in low birth weight infants (LBW) by passive immunization with SdrF mAb(s). LBW infants are defined as those infants born between 500-1500 g. Premature infants are born before a sufficient transfer of protective maternal antibodies through the placenta takes place. The combination of insufficient antibodies, blood losses for diagnostic purposes, less efficient phagocytosis, microbial intestinal overgrowth under selection pressure from antimicrobial treatment, and repeated invasion of otherwise sterile sites by indwelling catheters, are some of the reasons for the very high nosocomial infection rates in this vulnerable population.

It has been recently shown that *S. epidermidis* contains surface proteins structurally related to *S. aureus* MSCRAMMs, and numerous surface proteins from *S. epidermidis* have previously been disclosed, e.g., in U.S. Pat. Nos. 6,703,025 and 6,635,473, said patents incorporated herein by reference. One of these *S. epidermidis* proteins, called SdrF (serine-aspartate repeat protein F), has features typical of Gram-positive bacterial proteins that are anchored to the cell wall. This protein shows significant amino acid sequence homology to ClfA and ClfB from *S. aureus* including an 500-amino acid-long A region, a SD dipeptide repeat region, and features required for cell wall anchoring. However, it remains a desirable object to obtain effective methods of treating and/or preventing staphylococcal infections utilizing these surface proteins, and to obtain monoclonal antibodies which recognize a large number of strains of *S. epidermidis* so as to be widely effective in treating and/or preventing infection. To date, monoclonal antibodies that specifically recognize SdrF, exhibit high affinity ($>10^8$ $K_D$), and are protective in animals models of disease have not been described or suggested.

SUMMARY OF THE INVENTION

Accordingly, it is an object of the present invention to provide monoclonal antibodies that can bind to the SdrF protein from *S. epidermidis*, or certain subregions therein, with high affinity and which can thus be useful in methods to treat, prevent or diagnose staphylococcal infections.

It is also an object of the present invention to provide monoclonal antibodies which are able to bind SdrF and which are generated from the SdrF or the binding domain or A domain of the SdrF protein including its N1N2N3 regions, or other subdomains such as N2, N3, or N2N3, and which can be utilized in methods of treating or protecting against staphylococcal infections.

It is also an object of the present invention to provide monoclonal antibodies to the SdrF protein which can be useful in preventing adherence of Staphylococcal bacteria to host cells.

It is a further object of the present invention to provide antibodies and antisera which can recognize the binding domain of the SdrF protein and which can thus be useful in methods of treating, preventing, identifying or diagnosing staphylococcal infections.

These and other objects are provided by virtue of the present invention which comprises the generation and use of monoclonal antibodies which can recognize the *S. epidermidis* SdrF protein and/or its binding domains and subdomains, for the treatment or prevention of *Staphylococcus* infections. In accordance with the invention, suitable compositions and passive vaccines based on the monoclonal antibodies of the invention, as well as methods for their use, are also provided as set forth in the detailed description hereinbelow.

BRIEF DESCRIPTION OF THE DRAWING FIGURES

DETAILED DESCRIPTION OF THE PREFERRED EMBODIMENTS

Figure 1:
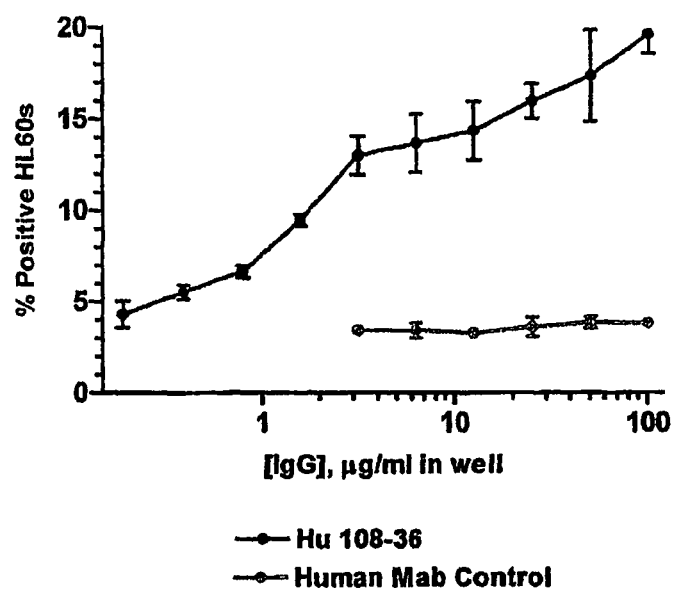
FIG. 1 is a graphic representation of fluorescent SdrF-coated Bead OP Assay with Humanized Anti-SdrF mAb.

In accordance with the present invention, there are provided monoclonal antibodies which can recognize and bind to the extracellular matrix binding protein SdrF, a surface localized protein from *S. epidermidis*, and subregions included therein including the N1, N2 and N3 regions, which together form the ligand binding A domain of SdrF, and combinations of these regions. In the preferred method of generating these monoclonal antibodies, they are raised against an *E. coli* expressed and purified SdrF (N1N2N3) protein used to generate a panel of murine monoclonal antibodies. However, monoclonal antibodies recognizing SdrF or its subregions can be raised from other subregions or larger parts of the protein as long as they are immunogenic and will be able to generate antibodies that recognize SdrF and/or its subregions.

In the preferred method of making monoclonal antibodies in accordance with the invention, these antibodies may be obtained in conventional ways including steps of introducing the SdrF antigen into a host animal, followed by isolation of sera and formation of a suitable hybridoma. In one such suitable method, a group of Balb/C mice received a series of subcutaneous immunizations of 1-10 mg of protein in solution or mixed with adjuvant. Seven days after each boost, serum was collected and titered in ELISA assays against MSCRAMMs or on whole cells (*S. epidermidis*). Three days after the final boost, the spleen was removed, teased into a single cell suspension and the lymphocytes harvested. The lymphocytes were then fused to a P3X63Ag8.653 myeloma cell line (ATCC #CRL-1580). Cell fusion, subsequent plating and feeding were performed according to the Production of Monoclonal Antibodies protocol from *Current Protocols in Immunology* (Chapter 2, Unit 2).

In the next step, screening and selection of Anti-SdrF monoclonal antibodies in accordance with the present invention took place. In this step, hybridomas generated from the fusion were screened for specific anti-SdrF antibody production using a standard ELISA assay. Positive clones were expanded and tested further for activity in a whole bacterial cell binding assay by flow cytometry and SdrF binding by BIACORE analysis. These clones were then subject to an ELISA analysis wherein immulon 2-HB high-binding 96-well microtiter plates (DYNEX) were coated with 1 µg/well of SdrF N1N2N3, N2N3, N2 or N3 in 1×PBS, pH 7.4 and incubated for 2 hours at room temperature. All washing steps in ELISAs were performed three times with 1×PBS, 0.05% TWEEN-20 wash buffer. Plates were washed and blocked with a 1% BSA solution at room temperature for 1 hour before hybridoma supernatant samples were added to wells. Plates were incubated with samples and relevant controls such as media alone for one hour at room temperature, washed, and goat anti-mouse IgG-AP (Sigma) diluted 1:5000 in 1×PBS, 0.05% TWEEN-20, 0.1% BSA was used as a secondary reagent. Plates were developed by addition of 1 mg/ml solution of 4-nitrophenyl phosphate (pNPP) (Sigma), followed by incubation at 37° C. for 30 minutes. Absorbance was read at 405 nm using a SPECTRAMAX 190 Plate Reader (Molecular Devices Corp.). Antibody supernatants that had an $OD_{405} \geq 3$ times above background (media alone, ~0.1 OD) were considered positive.

Throughout the BIACORE analysis, the flow rate remained constant at 10 ml/min. Prior to the SdrFN1N2N3 or SdrFN2N3 injection, test antibody was adsorbed to the chip via RAM-Fc binding. At time 0, SdrF (N1N2 or N1N2N3) at a concentration of 30 mg/ml was injected over the chip for 3 min followed by 2 minutes of dissociation. This phase of the analysis measured the relative association and disassociation kinetics of the Mab/SdrF interaction.

In addition to preparing monoclonal antibodies in accordance with the invention, polyclonal antiserum to SdrF was also generated and tested so as to be useful in comparisons of strain recognition with regard to the monoclonal antibodies of the invention. In this regard, polyclonal antiserum was generated by Strategic BioSolutions Inc. in New Zealand White SPF Rabbits using a standard immunization schedule. A primary subcutaneous immunization of 200 μg total SdrF protein with Complete Freund's adjuvant was administered on day 0. Boost immunizations of 200 μg total protein with Incomplete Freund's Adjuvant (IFA) were administered on days 21 and 35. The first test bleed was harvested on day 44, followed by an additional boost immunization on day 49, for a total of 4 immunizations. Test bleeds were then collected on days 58 and 63 with a final serum harvest on day 71. The IgG fraction was purified via protein A affinity chromatography and quantitated by OD280 uv-spectroscopy based on an extinction coefficient of 1.33.

The preparation of monoclonal antibodies in accordance with the invention and the generation of antiserum to SdrF was then subject to testing for binding to whole bacteria in flow experiments. In these experiments, S. epidermidis strain (9491) were collected, washed and incubated with mAb or PBS alone (control) at a concentration of 2 mg/ml after blocking with rabbit IgG (50 mg/ml). Following incubation with antibody (mAb and polyclonal), bacterial cells were incubated with Goat-$F_{(ab')2}$-Anti-Mouse-$F_{(ab')2}$-FITC which served as the detection antibody. After antibody labeling, bacterial cells were aspirated through the FACScaliber flow cytometer to analyze fluorescence emission (excitation: 488, emission: 570). For each bacterial strain, 10,000 events were collected and measured. The data showed that SdrF positive hybridomas were generated from 4 separate fusions (F108-F111). It was unusual to observe that all of the Biacore positive hybridomas were also positive for whole cell bacterial binding by flow cytometry; indicating that the recombinant A domain construct (SdrF N1N2N3) expressed and purified from E. coli mirrored the native antigen on the bacterial cell surface. The flow analysis of cell surface bacterial cell staining demonstrated that the anti-SdrF monoclonals and polyclonal anti-sera stained with equal intensity and frequency for the greater than 20 S. epidermidis strains tested. The analysis also indicated that SdrF has immunogenic epitopes that include the N2 and N3 domains linked (110-15) as well as the N2 (108-36) and N3 (108-1) domains alone. The unique globular domains of N2 and N3 as well as the tertiary conformational structure with N2N3, create epitopes for high affinity interaction with monoclonal antibodies on purified recombinant protein as well as on bacterial cells.

Accordingly, the present invention provides monoclonal antibodies which recognize the SdrF protein and which can bind to S. epidermidis so as to be useful in methods of treating, preventing or diagnosing staphylococcal infections. In addition, the invention provides monoclonals that can recognize subdomains of SdrF, namely ones that can recognize N2, ones that recognize N3, and ones that recognize the N2N3 combined domain as described herein. Accordingly, the present invention contemplates these monoclonal antibodies, and other monoclonals recognizing the same epitopes of the specific monoclonals described herein.

Accordingly, the present invention relates to an isolated and/or purified monoclonal antibody which can bind to the SdrF protein and/or their binding subdomains, and which thus can be useful in methods of inhibiting adherence of S. epidermidis to host cells and thus treat or prevent a staphylococcal infection when used in amounts effective to prevent or treat such infections. In addition to the methods described above, these monoclonal antibodies may be produced using any of a variety of conventional methods, e.g., the method of Kohler and Milstein, Nature 256:495-497 (1975), or other suitable ways known in the field. In addition, it will be recognized that these monoclonals can be prepared in a number of forms, including chimeric, humanized, or human in addition to murine in ways that would be well known in this field. Still further, monoclonal antibodies may be prepared from a single chain, such as the light or heavy chains, and in addition may be prepared from active fragments of an antibody which retain the binding characteristics (e.g., specificity and/or affinity) of the whole antibody. By active fragments is meant an antibody fragment which has the same binding specificity as a complete antibody which binds to extracellular matrix binding proteins, and the term "antibody" as used herein is meant to include said fragments. Additionally, antisera prepared using monoclonal or polyclonal antibodies in accordance with the invention are also contemplated and may be prepared in a number of suitable ways as would be recognized by one skilled in the art.

Although production of antibodies as indicated above is preferably carried out using synthetic or recombinantly produced forms of the SdrF protein or antigenic subregions therefrom, antibodies may also be generated from natural isolated and purified SdrF proteins or subregions, or active fragments thereof. Still other conventional ways are available to generate the SdrF antibodies of the present invention using recombinant or natural purified SdrF proteins or their active regions, as would be recognized by one skilled in the art.

As would be recognized by one skilled in the art, the antibodies of the present invention may also be formed into suitable pharmaceutical compositions, for administration to a human or animal patient in order to treat or prevent an infection caused by staphylococcal bacteria. Pharmaceutical compositions containing the antibodies of the present invention, or effective fragments thereof, may be formulated in combination with any suitable pharmaceutical vehicle, excipient or carrier that would commonly be used in this art, including such conventional materials for this purpose, e.g., saline, dextrose, water, glycerol, ethanol, other therapeutic compounds, and combinations thereof. As one skilled in this art would recognize, the particular vehicle, excipient or carrier used will vary depending on the patient and the patient's condition, and a variety of modes of administration would be suitable for the compositions of the invention, as would be recognized by one of ordinary skill in this art. Suitable methods of administration of any pharmaceutical composition disclosed in this application include, but are not limited to, topical, oral, anal, vaginal, intravenous, intraperitoneal, intramuscular, subcutaneous, intranasal and intradermal administration.

If topical administration is desired, the composition may be formulated as needed in a suitable form, e.g., an ointment, cream, gel, lotion, drops (such as eye drops and ear drops), or solution (such as mouthwash). Wound or surgical dressings, sutures and aerosols may be impregnated with the composition. The composition may contain conventional additives, such as preservatives, solvents to promote penetration, and emollients. Topical formulations may also contain conventional carriers such as cream or ointment bases, ethanol, or oleyl alcohol.

Additional forms of antibody compositions, and other information concerning compositions, methods and applications with regard to the MSCRAMM® SdrF of the present invention can also be found from other patent references concerning other MSCRAMM®s which will generally be applicable to the present invention as well, and these patents include U.S. Pat. Nos. 7,045,131; 6,994,855; 6,979,446; 6,841,154; 6,703,025; 6,692,739; 6,685,943; 6,680,195;

6,635,473; 6,288,214; 6,177,084; and 6,008,341, all of said patents incorporated herein by reference.

The antibody compositions of the present invention which are generated against the N1N2N3 regions from the SdrF protein from *S. epidermidis* may also be administered with a suitable adjuvant in an amount effective to enhance the immunogenic response against the conjugate. For example, suitable adjuvants may include alum (aluminum phosphate or aluminum hydroxide), which is used widely in humans, and other adjuvants such as saponin and its purified component Quil A, Freund's complete adjuvant, RIBBI adjuvant, and other adjuvants used in research and veterinary applications. Still other chemically defined preparations such as muramyl dipeptide, monophosphoryl lipid A, phospholipid conjugates such as those described by Goodman-Snitkoff et al. *J. Immunol.* 147: 410-415 (1991) and incorporated by reference herein, encapsulation of the conjugate within a proteoliposome as described by Miller et al., *J. Exp. Med.* 176:1739-1744 (1992) and incorporated by reference herein, and encapsulation of the protein in lipid vesicles such as NOVASOME® lipid vesicles (Micro Vescular Systems, Inc., Nashua, N.H.) may also be useful.

The antibody compositions of the present invention will thus be useful for interfering with, modulating, or inhibiting binding interactions between the SdrF protein on coagulase-negative staphylococcal bacteria and its ligand on host cells and tissues, and will thus have particular applicability in developing compositions and methods of preventing or treating staphylococcal infection, and in inhibiting binding of staphylococcal bacteria to host tissue and/or cells.

In accordance with the present invention, methods are provided for preventing or treating a staphylococcal infection which comprise administering an effective amount of the monoclonal antibody of the present invention as described above in amounts effective to treat or prevent the infection. In addition, these monoclonal antibodies have been shown to have high affinity in binding of staphylococcal bacteria, and thus should be effective in treating or preventing infection from staph bacteria such as *S. epidermidis*. Further, these monoclonals will be useful in inhibiting *S. epidermidis* biding to the extracellular matrix of the host, and in reducing or eliminating the adherence of *S. epidermidis* on host cells or on other surfaces, e.g., medical equipment, implants or prosthetics.

Accordingly, in accordance with the invention, administration of the antibodies of the present invention in any of the conventional ways described above (e.g., topical, parenteral, intramuscular, etc.), and will thus provide an extremely useful method of treating or preventing staphylococcal infections in human or animal patients. By effective amount is meant that level of use, such as of an antibody titer, that will be sufficient to either prevent adherence of the bacteria, to inhibit binding of staph bacteria to host cells and thus be useful in the treatment or prevention of a staph infection. As would be recognized by one of ordinary skill in this art, the level of antibody titer needed to be effective in treating or preventing staphylococcal infection will vary depending on the nature and condition of the patient, and/or the severity of the pre-existing staphylococcal infection.

In addition to the use of antibodies of the present invention to treat or prevent *S. epidermidis* infection as described above, the present invention contemplates the use of these antibodies in a variety of ways, including the detection of the presence of *S. epidermidis* to diagnose a staph infection, whether in a patient or on medical equipment, implants or prosthetics which may also become infected. In accordance with the invention, a preferred method of detecting the presence of staph infections involves the steps of obtaining a sample suspected of being infected by one or more staphylococcal bacteria species or strains, such as a sample taken from an individual, for example, from one's blood, saliva, tissues, bone, muscle, cartilage, or skin. The cells can then be lysed, and the DNA extracted, precipitated and amplified. Following isolation of the sample, diagnostic assays utilizing the antibodies of the present invention may be carried out to detect the presence of *S. epidermidis*, and such assay techniques for determining such presence in a sample are well known to those skilled in the art and include methods such as radioimmunoassay, Western blot analysis and ELISA assays. In general, in accordance with the invention, a method of diagnosing an *S. epidermidis* infection is contemplated wherein a sample suspected of being infected with *S. epidermidis* infection has added to it the monoclonal antibody in accordance with the present invention, and *S. epidermidis* is indicated by antibody binding to the SdrF proteins in the sample.

Accordingly, antibodies in accordance with the invention may be used for the specific detection or diagnosis of staphylococcal proteins, for the prevention of infection from staph bacteria, for the treatment of an ongoing infection, or for use as research tools. The term "antibodies" as used herein includes monoclonal, polyclonal, chimeric, single chain, bispecific, simianized, and humanized or primatized antibodies as well as Fab fragments, such as those fragments which maintain the binding specificity of the antibodies to the SdrF proteins, including the products of an Fab immunoglobulin expression library. Accordingly, the invention contemplates the use of single chains such as the variable heavy and light chains of the antibodies as will be set forth below. Generation of any of these types of antibodies or antibody fragments is well known to those skilled in the art. In the present case, monoclonal antibodies to SdrF proteins have been generated against its ligand binding domain A (made up of subregions N1, N2 and N3) and have been isolated and shown to have high affinity to *S. epidermidis*. Moreover, the monoclonals of the present invention have been shown to recognize a high number of strains, on an equivalent level to that recognize by polyclonal antibodies to SdrF, and thus can be used effectively in methods to protect against staphylococcal infection or treat same.

When so desired for medical or research purposes, any of the above described antibodies may be labeled directly with a detectable label for identification and quantification of staph bacteria. Labels for use in immunoassays are generally known to those skilled in the art and include enzymes, radioisotopes, and fluorescent, luminescent and chromogenic substances, including colored particles such as colloidal gold or latex beads. Suitable immunoassays include enzyme-linked immunosorbent assays (ELISA).

Alternatively, the antibody may be labeled indirectly by reaction with labeled substances that have an affinity for immunoglobulin. The antibody may be conjugated with a second substance and detected with a labeled third substance having an affinity for the second substance conjugated to the antibody. For example, the antibody may be conjugated to biotin and the antibody-biotin conjugate detected using labeled avidin or streptavidin. Similarly, the antibody may be conjugated to a hapten and the antibody-hapten conjugate detected using labeled anti-hapten antibody. These and other methods of labeling antibodies and assay conjugates are well known to those skilled in the art.

Antibodies to SdrF as described above may also be used in production facilities or laboratories to isolate additional quantities of the proteins, such as by affinity chromatography.

For example, the antibodies of the invention may also be utilized to isolate additional amounts of the SdrF proteins or their active fragments.

The isolated antibodies of the present invention, or active fragments thereof, may also be utilized in the development of vaccines for passive immunization against staph infections. Further, when administered as pharmaceutical composition to a wound or used to coat medical devices or polymeric biomaterials in vitro and in vivo, the antibodies of the present invention, may be useful in those cases where there is a previous staph infection because of the ability of this antibody to further restrict and inhibit S. epidermidis binding to fibronectin and thus limit the extent and spread of the infection. In addition, the antibody may be modified as necessary so that, in certain instances, it is less immunogenic in the patient to whom it is administered. For example, if the patient is a human, the antibody may be "humanized" by transplanting the complementarity determining regions (CDR's) of the hybridoma-derived antibody into a human monoclonal antibody as described, e.g., by Jones et al., Nature 321:522-525 (1986) or Tempest et al. Biotechnology 9:266-273 (1991) or "veneered" by changing the surface exposed murine framework residues in the immunoglobulin variable regions to mimic a homologous human framework counterpart as described, e.g., by Padlan, Molecular Imm. 28:489-498 (1991) and U.S. Pat. No. 6,797,492, all of these references incorporated herein by reference. Even further, when so desired, the monoclonal antibodies of the present invention may be administered in conjunction with a suitable antibiotic to further enhance the ability of the present compositions to fight bacterial infections.

As indicated above, staphylococcal infections are not only a problem with patients but also may affect medical devices, implants and prosthetics, and thus the present invention can be utilized to protect these devices from staphylococcal infection as well, e.g., by coating these devices with the compositions of the present invention. Medical devices or polymeric biomaterials to be coated with the antibody compositions described herein include, but are not limited to, staples, sutures, replacement heart valves, cardiac assist devices, hard and soft contact lenses, intraocular lens implants (anterior chamber or posterior chamber), other implants such as corneal inlays, kerato-prostheses, vascular stents, epikeratophalia devices, glaucoma shunts, retinal staples, scleral buckles, dental prostheses, thyropolastic devices, laryngoplastic devices, vascular grafts, soft and hard tissue prostheses including, but not limited to, pumps, electrical devices including stimulators and recorders, auditory prostheses, pacemakers, artificial larynx, dental implants, mammary implants, other implants, cranio/facial tendons, artificial joints, tendons, ligaments, menisci, and disks, artificial bones, artificial organs including artificial pancreas, artificial hearts, artificial limbs, and heart valves; stents, wires, guide wires, intravenous and central venous catheters, laser and balloon angioplasty devices, vascular and heart devices (tubes, catheters, balloons), ventricular assists, blood dialysis components, blood oxygenators, urethral/ureteral/urinary devices (Foley catheters, stents, tubes and balloons), airway catheters (endrotracheal and tracheostomy tubes and cuffs), enteral feeding tubes (including nasogastric, intragastric and jejunal tubes), wound drainage tubes, tubes used to drain the body cavities such as the pleural, peritoneal, cranial, and pericardial cavities, blood bags, test tubes, blood collection tubes, vacutainers, syringes, needles, pipettes, pipette tips, and blood tubing.

It will be understood by those skilled in the art that the term "coated" or "coating", as used herein, means to apply the antibody or pharmaceutical composition derived therefrom, to a surface of the device, preferably an outer surface that would be exposed to streptococcal bacterial infection. The surface of the device need not be entirely covered by the protein, antibody or active fragment.

In a preferred embodiment, the antibodies may also be used as a passive vaccine which will be useful in providing suitable antibodies to treat or prevent a staphylococcal infection. As would be recognized by one skilled in this art, a vaccine may be packaged for administration in a number of suitable ways, such as by parenteral (i.e., intramuscular, intradermal or subcutaneous) administration or nasopharyngeal (i.e., intranasal) administration. One such mode is where the vaccine is injected intramuscularly, e.g., into the deltoid muscle, however, the particular mode of administration will depend on the nature of the bacterial infection to be dealt with and the condition of the patient. The vaccine is preferably combined with a pharmaceutically acceptable carrier to facilitate administration, and the carrier is usually water or a buffered saline, with or without a preservative. The vaccine may be lyophilized for resuspension at the time of administration or in solution.

The preferred dose for administration of an antibody composition in accordance with the present invention is that amount will be effective in preventing of treating a staphylococcal infection, and one would readily recognize that this amount will vary greatly depending on the nature of the infection and the condition of a patient. As indicated above, an "effective amount" of antibody or pharmaceutical agent to be used in accordance with the invention is intended to mean a nontoxic but sufficient amount of the agent, such that the desired prophylactic or therapeutic effect is produced. As will be pointed out below, the exact amount of the antibody or a particular agent that is required will vary from subject to subject, depending on the species, age, and general condition of the subject, the severity of the condition being treated, the particular carrier or adjuvant being used and its mode of administration, and the like. Accordingly, the "effective amount" of any particular antibody composition will vary based on the particular circumstances, and an appropriate effective amount may be determined in each case of application by one of ordinary skill in the art using only routine experimentation. The dose should be adjusted to suit the individual to whom the composition is administered and will vary with age, weight and metabolism of the individual. The compositions may additionally contain stabilizers or pharmaceutically acceptable preservatives, such as thimerosal (ethyl (2-mercaptobenzoate-S)mercury sodium salt) (Sigma Chemical Company, St. Louis, Mo.).

When used with suitable labels or other appropriate detectable biomolecule or chemicals, the monoclonal antibodies described herein are useful for purposes such as in vivo and in vitro diagnosis of staphylococcal infections or detection of staphylococcal bacteria. Laboratory research may also be facilitated through use of such antibodies. Various types of labels and methods of conjugating the labels to the antibodies of the invention are well known to those skilled in the art, such as the ones set forth below.

For example, the antibody can be conjugated (directly or via chelation) to a radiolabel such as, but not restricted to, $^{32}P$, $^{3}H$, $^{14}C$, $^{35}S$, $^{125}I$, or $^{131}I$. Detection of a label can be by methods such as scintillation counting, gamma ray spectrometry or autoradiography. Bioluminescent labels, such as derivatives of firefly luciferin, are also useful. The bioluminescent substance is covalently bound to the protein by conventional methods, and the labeled protein is detected when an enzyme, such as luciferase, catalyzes a reaction with ATP causing the bioluminescent molecule to emit photons of light. Fluorogens may also be used to label proteins. Examples of fluorogens include fluorescein and derivatives, phycoerythrin, allo-phycocyanin, phycocyanin, rhodamine, and Texas Red. The fluorogens are generally detected by a fluorescence detector.

The location of a ligand in cells can be determined by labeling an antibody as described above and detecting the label in accordance with methods well known to those skilled in the art, such as immunofluorescence microscopy using procedures such as those described by Warren et al. (*Mol. Cell. Biol.,* 7: 1326-1337, 1987).

As indicated above, the monoclonal antibodies of the present invention, or active portions or fragments thereof, are particularly useful for interfering with the initial physical interaction between a staphylococcal pathogen responsible for infection and a mammalian host, such as the adhesion of the bacteria to mammalian extracellular matrix proteins, and this interference with physical interaction may be useful both in treating patients and in preventing or reducing bacteria infection on in-dwelling medical devices to make them safer for use.

In another embodiment of the present invention, a kit which may be useful in isolating and identifying staphylococcal bacteria and infection is provided which comprises the antibodies of the present invention in a suitable form, such as lyophilized in a single vessel which then becomes active by addition of an aqueous sample suspected of containing the staphylococcal bacteria. Such a kit will typically include a suitable container for housing the antibodies in a suitable form along with a suitable immunodetection reagent which will allow identification of complexes binding to the SdrF antibodies of the invention. For example, the immunodetection reagent may comprise a suitable detectable signal or label, such as a biotin or enzyme that produces a detectable color, etc., which normally may be linked to the antibody or which can be utilized in other suitable ways so as to provide a detectable result when the antibody binds to the antigen.

In short, the antibodies of the present invention which bind to the SdrF protein or active fragments or subregions thereof are thus extremely useful in treating or preventing staphylococcal infections in human and animal patients and in medical or other in-dwelling devices. Accordingly, the present invention relates to methods of identifying and isolating antibodies which can bind to SdrF and which can be used in methods of treatment of staph infections which involve opsonophagocytic killing of the bacteria. Antibodies which are identified and/or isolated using the present method, such as the antibodies which can bind to the SdrF protein or its subregions and which can prevent or treat a staph infection, and antibodies recognizing the same epitopes as those recognized by the monoclonals described herein, are thus a part of the present invention.

EXAMPLES

The following examples are provided which exemplify aspects of the preferred embodiments of the present invention. It should be appreciated by those of skill in the art that the techniques disclosed in the examples which follow represent techniques discovered by the inventors to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

Example 1

Expression and Purification of SdrF Proteins

To characterize the utility of this invention, domains of the SdrF protein were cloned, expressed recombinantly and purified. SdrF N1N2N3 (52-679) represents the putative A domain of the SdrF gene. SdrF N2N3 (361-679) represents the putative sub-domain required for ECM binding based on Sdr family homology. SdrF N2 (361-517) and N3 (517-679) represent sub-domains of the putative ECM binding domain.

The actual sequence of the SdrF A domain (subregions N1, N2 and N3) is as follows:
SdrF N1N2N3 (52-679):

```
Nucleotide Sequence
                                          (SEQ ID NO: 1)
GCTGAAGACAATCAATTAGAATCAGCTTCAAAAGAAGAACAGAAAGGTAG

TCGTGATAATGAAAACTCAAAACTTAATCAAGTCGATTTAGACAACGGAT

CACATAGTTCTGAGAAAACAACAAATGTAAACAATGCAACTGAAGTAAAA

AAAGTTGAAGCACCAACGACAAGTGACGTATCTAAGCCTAAAGCTAATGA

AGCAGTAGTGACGAATGAGTCAACTAAACCAAAAACAACAGAAGCACCAA

CTGTTAATGAGGAATCAATAGCTGAAACACCCAAAACCTCAACTACACAA

CAAGATTCGACTGAGAAGAATAATCCATCTTTAAAAGATAATTTAAATTC

ATCCTCAACGACATCTAAAGAAAGTAAAACAGACGAACATTCTACTAAGC

AAGCTCAAATGTCTACTAATAAATCAAATTTAGACACAAATGACTCTCCA

ACTCAAAGTGAGAAAACTTCATCACAAGCAAATAACGACAGTACAGATAA

TCAGTCAGCACCTTCTAAACAATTAGATTCAAAACCATCAGAACAAAAAG

TATATAAAACAAAATTTAATGATGAACCTACTCAAGATGTTGAACACACG

ACAACTAAATTAAAAACACCTTCTGTTTCAACAGATAGTTCAGTCAATGA

TAAGCAAGATTACACACGAAGTGCTGTAGCTAGTTTAGGTGTTGATTCTA

ATGAAACAGAAGCAATTACAAATGCAGTTAGAGACTAATTTAGATTTAAA

AGCTGCATCTAGAGAACAAATCAATGAAGCAATCATTGCTGAAGCACTAA

AAAAAGACTTTTCTAACCCTGATTATGGTGTCGATACGCCATTAGCTCTA

AACAGATCTCAATCAAAAAATTCACCACATAAGAGTGCAAGTCCACGCAT

GAATTTAATGAGTTTAGCTGCTGAGCCTAATAGTGGTAAAAATGTGAATG

ATAAAGTTAAAATCACAAACCCTACGCTTTCACTTAATAAGAGTAATAAT

CACGCTAATAACGTAATATGGCCAACAAGTAACGAACAATTTAATTTAAA

AGCAAATTATGAATTAGATGACAGCATAAAAGAGGGAGATACTTTTACTA

TTAAGTATGGTCAGTATATTAGACCGGGTGGTTTAGAACTTCCTGCAATA

AAAACTCAACTACGTAGTAAGGATGGCTCTATTGTAGCTAATGGTGTATA

TGATAAAACTACAAATACGACGACTTATACATTTACTAACTATGTTGATC

AATATCAAAATATTACAGGTAGTTTTGATTTAATTGCGACGCCTAAGAGG

GAAACAGCAATTAAGGATAATCAGAATTATCCTATGGAAGTGACGATTGC

TAACGAAGTAGTCAAAAAAGACTTCATTGTGGATTATGGTAATAAAAAGG
```

```
ACAATACAACTACAGCAGCGGTAGCAAATGTGGATAATGTAAATAATAAA
CATAACGAAGTTGTTTATCTAAACCAAAATAACCAAAACCCTAAATATGC
TAAATATTTCTCAACAGTAAAAAATGGTGAATTTATACCAGGTGAAGTGA
AAGTTTACGAAGTGACGGATACCAATGCGATGGTAGATAGCTTCAATCCT
GATTTAAATAGTTCTAATGTAAAAGATGTGACAAGTCAATTTGCACCTAA
AGTAAGTGCAGATGGTACTAGAGTTGATATCAATTTTGCTAGAAGTATGG
CAAATGGTAAAAAGTATATTGTAACTCAAGCAGTGAGACCAACGGGAACT
GGAAATGTTTATACCGAATATTGGTTAACAAGAGATGGTACTACCAATAC
AAATGATTTTTACCGTGGAACGAAGTCTACAACGGTGACTTATCTCAATG
GTTCTTCAACAGCACAGGGGGATAATCCT
```

Amino Acid Sequence
(SEQ ID NO: 2)
```
AEDNQLESASKEEQKGSRDNENSKLNQVDLDNGSHSSEKTTNVNNATEVK
KVEAPTTSDVSKPKANEAWTNESTKPKTTEAPTVNEESIAETPKTSTTQQ
DSTEKNNPSLKDNLNSSSTTSKESKTDEHSTKQAQMSTNKSNLDTNDSPT
QSEKTSSQANNDSTDNQSAPSKQLDSKPSEQKVYKTKFNDEPTQDVEHTT
TKLKTPSVSTDSSVNDKQDYTRSAVASLGVDSNETEAITNAVRDNLDLKA
ASREQINEAIIAEALKKDFSNPDYGVDTPLALNRSQSKNSPHKSASPRMN
LMSLAAEPNSGKNVNDKVKITNPTLSLNKSNNHANNVIWPTSNEQFNLKA
NYELDDSIKEGDTFTIKYGQYIRPGGLELPAIKTQLRSKDGSIVANGVYD
KTTNTTTYTFTNYVDQYQNITGSFDLIATPKRETAIKDNQNYPMEVTIAN
EVVKKDFIVDYGNKKDNTTTAAVANVDVNNKHNEVVYLNQNNQNPKYAK
YFSTVKNGEFIPGEVKVYEVTDTNAMVDSFNPDLNSSNVKDVTSQFAPKV
SADGTRVDINFARSMANGKKYIVTQAVRPTGTGNVYTEYWLTRDGTTNTN
DFYRGTKSTTVTYLNGSSTAQGDNP
```

The SdrF N1 region is from amino acids 52-361 of the SdrF protein, SdrF N2 is from amino acids 361-517, and SdrF N3 is from amino acids 517-679.

The expression sequence of the SdrF A domain and subregions N1, N2 and N3 as used in the examples of the invention are as follows:

SdrF Expression Sequences and Proteins
SdrF N1N2N3 (52-679):

Nucleotide Sequence
(SEQ ID NO: 3)
```
ATGAGAGGATCGCATCACCATCACCATCACGGATCCGCTGAAGACAATCA
ATTAGAATCAGCTTCAAAAGAAGAACAGAAAGGTAGTCGTGATAATGAAA
ACTCAAAACTTAATCAAGTCGATTTAGACAACGGATCACATAGTTCTGAG
AAAACAACAAATGTAAACAATGCAACTGAAGTAAAAAAAGTTGAAGCACC
AACGACAAGTCACGTATCTAAGCCTAAAGCTAATGAAGCAGTAGTGACGA
ATGAGTCAACTAAACCAAAAACAACAGAAGCACCAACTGTTAATGAGGAA
TCAATAGCTGAAACACCCAAAACCTCAACTACACAACAAGATTCGACTGA
GAAGAATAATCCATCTTTAAAAGATAATTTAAATTCATCCTCAACGACAT
CTAAAGAAAGTAAAACAGACGAACATTCTACTAAGCAAGCTCAAATGTCT
ACTAATAAATCAAATTTAGACACAAATGACTCTCCAACTCAAAGTGAGAA
AACTTCATCACAAGCAAATAACGACAGTACAGATAATCAGTCAGCACCTT
CTAAACAATTAGATTCAAAACCATCAGAACAAAAAGTATATAAAACAAAA
TTTAATGATGAACCTACTCAAGATGTTGAACACACGACAACTAAATTAAA
AACACCTTCTGTTTCAACAGATAGTTCAGTCAATGATAAGCAAGATTACA
CACGAAGTGCTGTAGCTAGTTTAGGTGTTGATTCTAATGAAACAGAAGCA
ATTACAAATGCAGTTAGAGACAATTTAGATTTAAAAGCTGCATCTAGAGA
ACAAATCAATGAAGCAATCATTGCTGAAGCACTAAAAAAAGACTTTTCTA
ACCCTGATTATGGTGTCGATACGCCATTAGCTCTAAACAGATCTCAATCA
AAAAATTCACCACATAAGAGTGCAAGTCCACGCATGAATTTAATGAGTTT
AGCTGCTGAGCCTAATAGTGGTAAAAATGTGAATGATAAAGTTAAAATCA
CAAACCCTACGCTTTCACTTAATAAGAGTAATAATCACGCTAATAACGTA
ATATGGCCAACAAGTAACGAACAATTTAATTTAAAAGCAAATTATGAATT
AGATGACAGCATAAAAGAGGGAGATACTTTTACTATTAAGTATGGTCAGT
ATATTAGACCGGGTGGTTTAGAACTTCCTGCAATAAAAACTCAACTACGT
AGTAAGGATGGCTCTATTGTAGCTAATGGTGTATATGATAAAACTACAAA
TACGACGACTTATACATTTACTAACTATGTTGATCAATATCAAAATATTA
CAGGTAGTTTTGATTTAATTGCGACGCCTAAGAGGGAAACAGCAATTAAG
GATAATCAGAATTATCCTATGGAAGTGACGATTGCTAACGAAGTAGTCAA
AAAAGACTTCATTGTGGATTATGGTAATAAAAAGGACAATACAACTACAG
CAGCGGTAGCAAATGTGGATAATGTAAATAATAAACATAACGAAGTTGTT
TATCTAAACCAAAATAACCAAAACCCTAAATATGCTAAATATTTCTCAAC
AGTAAAAAATGGTGAATTTATACCAGGTGAAGTGAAAGTTTACGAAGTGA
CGGATACCAATGCGATGGTAGATAGCTTCAATCCTGATTTAAATAGTTCT
AATGTAAAAGATGTGACAAGTCAATTTGCACCTAAAGTAAGTGCAGATGG
TACTAGAGTTGATATCAATTTTGCTAGAAGTATGGCAAATGGTAAAAAGT
ATATTGTAACTCAAGCAGTGAGACCAACGGGAACTGGAAATGTTTATACC
GAATATTGGTTAACAAGAGATGGTACTACCAATACAAATGATTTTTACCG
TGGAACGAAGTCTACAACGGTGACTTATCTCAATGGTTCTTCAACAGCAC
AGGGGGATAATCCTTGA
```

Amino Acid Sequence
(SEQ ID NO: 4)
<u>MRGSHHHHHHGS</u>AEDNQLESASKEEQKGSRDNENSKLNQVDLDNGSHSSE
KTTNVNNATEVKKVEAPTTSDVSKPKANEAVVTNESTKPKTTEAPTVNEE
SIAETPKTSTTQQDSTEKNNPSLKDNLNSSSTTSKESKTDEHSTKQAQMS
TNKSNLDTNDSPTQSEKTSSQANNDSTDNQSAPSKQLDSKPSEQKVYKTK
FNDEPTQDVEHTTTKLKTPSVSTDSSVNDKQDYTRSAVASLGVDSNETEA
ITNAVRDNLDLKAASREQINEAIIAEALKKDFSNPDYGVDTPLALNRSQS
KNSPHKSASPRMNLMSLAAEPNSGKNVNDKVKITNPTLSLNKSNNHANNV
IWPTSNEQFNLKANYELDDSIKEGDTFTIKYGQYIRPGGLELPAIKTQLR
SKDGSIVANGVYDKTTNTTTYTFTNYVDQYQNITGSFDLIATPKRETAIK
DNQNYPMEVTIANEWKKDFIVDYGNKKDNTTTAAVANVDVNNKHNEWYL

NQNNQNPKYAKYFSTVKNGEFIPGEVKVYEVTDTNAMVDSFNPDLNSSNV

KDVTSQFAPKVSADGTRVDINFARSMANGKKYIVTQAVRPTGTGNVYTEY

WLTRDGTTNTNDFYRGTKSTTVTYLNGSSTAQGDNP
Underlined sequence represents the purification
tag generated from the PQE-30 expression vector.

SdrF N2N3 (361-679):

Nucleotide Sequence
(SEQ ID NO: 5)
ATGAGAGGATCGCATCACCATCACCATCACGGATCCCCTAATAGTGGTAA

AAATGTGAATGATAAAGTTAAAATCACAAACCCTACGCTTTCACTTAATA

AGAGTAATAATCACGCTAATAACGTAATATGGCCAACAAGTAACGAACAA

TTTAATTTAAAAGCAAATTATGAATTAGATGACAGCATAAAAGAGGGAGA

TACTTTTACTATTAAGTATGGTCAGTATATTAGACCGGGTGGTTTAGAAC

TTCCTGCAATAAAAACTCAACTACGTAGTAAGGATGGCTCTATTGTAGCT

AATGGTGTATATGATAAAACTACAAATACGACGACTTATACATTTACTAA

CTATGTTGATCAATATCAAAATATTACAGGTAGTTTTGATTTAATTGCGA

CGCCTAAGAGGGAAACAGCAATTAAGGATAATCAGAATTATCCTATGGAA

GTGACGATTGCTAACGAAGTAGTCAAAAAAGACTTCATTGTGGATTATGG

TAATAAAAAGGACAATACAACTACAGCAGCGGTAGCAAATGTGGATAATG

TAAATAATAAACATAACGAAGTTGTTTATCTAAACCAAAATAACCAAAAC

CCTAAATATGCTAAATATTTCTCAACAGTAAAAAATGGTGAATTTATACC

AGGTGAAGTGAAAGTTTACGAAGTGACGGATACCAATGCGATGGTAGATA

GCTTCAATCCTGATTTAAATAGTTCTAATGTAAAAGATGTGACAAGTCAA

TTTGCACCTAAAGTAAGTGCAGATGGTACTAGAGTTGATATCAATTTTGC

TAGAAGTATGGCAAATGGTAAAAAGTATATTGTAACTCAAGCAGTGAGAC

CAACGGGAACTGGAAATGTTTATACCGAATATTGGTTAACAAGAGATGGT

ACTACCAATACAAATGATTTTTACCGTGGAACGAAGTCTACAACGGTGAC

TTATCTCAATGGTTCTTCAACAGCACAGGGGGATAATCCTTGA

Amino Acid Sequence
(SEQ ID NO: 6)
MRGSHHHHHHGSPNSGKNVNDKVKITNPTLSLNKSNNHANNVIWPTSNEQ

FNLKANYELDDSIKEGDTFTIKYGQYIRPGGLELPAIKTQLRSKDGSIVA

NGVYDKTTNTTTYTFTNYVDQYQNITGSFDLIATPKRETAIKDNQNYPME

VTIANEWKKDFIVDYGNKKDNTTTAAVANVDNVNNKHNEVVYLNQNNQNP

KYAKYFSTVKNGEFIPGEVKVYEVTDTNAMVDSFNPDLNSSNVKDVTSQF

APKVSADGTRVDINFARSMANGKKYIVTQAVRPTGTGNVYTEYWLTRDGT

TNTNDFYRGTKSTTVTYLNGSSTAQGDNP
Underlined sequence represents the purification
tag generated from the PQE-30 expression vector.

SdrF N1N2 (52-517):

Nucleotide Sequence
(SEQ ID NO: 7)
ATGAGAGGATCGCATCACCATCACCATCACGGATCCGCTGAAGACAATCA

ATTAGAATCAGCTTCAAAAGAAGAACAGAAAGGTAGTCGTGATAATGAAA

ACTCAAAACTTAATCAAGTCGATTTAGACAACGGATCACATAGTTCTGAG

AAAACAACAAATGTAAACAATGCAACTGAAGTAAAAAAAGTTGAAGCACC

AACGACAAGTGACGTATCTAAGCCTAAAGCTAATGAAGCAGTAGTGACGA

ATGAGTCAACTAAACCAAAAACAACAGAAGCACCAACTGTTAATGAGGAA

TCAATAGCTGAAACACCCAAAACCTCAACTACACAACAAGATTCGACTGA

GAAGAATAATCCATCTTTAAAAGATAATTTAAATTCATCCTCAACGACAT

CTAAAGAAAGTAAAACAGACGAACATTCTACTAAGCAAGCTCAAATGTCT

ACTAATAAATCAAATTTAGACACAAATGACTCTCCAACTCAAAGTGAGAA

AACTTCATCACAAGCAAATAACGACAGTACAGATAATCAGTCAGCACCTT

CTAAACAATTAGATTCAAAACCATCAGAACAAAAAGTATATAAAACAAAA

TTTAATGATGAACCTACTCAAGATGTTGAACACACGACAACTAAATTAAA

AACACCTTCTGTTTCAACAGATAGTTCAGTCAATGATAAGCAAGATTACA

CACGAAGTGCTGTAGCTAGTTTAGGTGTTGATTCTAATGAAACAGAAGCA

ATTACAAATGCAGTTAGAGACAATTTAGATTTAAAAGCTGCATCTAGAGA

ACAAATCAATGAAGCAATCATTGCTGAAGCACTAAAAAAAGACTTTTCTA

ACCCTGATTATGGTGTCGATACGCCATTAGCTCTAAACAGATCTCAATCA

AAAAATTCACCACATAAGAGTGCAAGTCCACGCATGAATTTAATGAGTTT

AGCTGCTGAGCCTAATAGTGGTAAAAATGTGAATGATAAAGTTAAAATCA

CAAACCCTACGCTTTCACTTAATAAGAGTAATAATCACGCTAATAACGTA

ATATGGCCAACAAGTAACGAACAATTTAATTTAAAAGCAAATTATGAATT

AGATGACAGCATAAAAGAGGGAGATACTTTTACTATTAAGTATGGTCAGT

ATATTAGACCGGGTGGTTTAGAACTTCCTGCAATAAAAACTCAACTACGT

AGTAAGGATGGCTCTATTGTAGCTAATGGTGTATATGATAAAACTACAAA

TACGACGACTTATACATTTACTAACTATGTTGATCAATATCAAAATATTA

CAGGTAGTTTTGATTTAATTGCGACGCCTAAGAGGGAAACAGCAATTAAG

GATAATCAGAATTATCCTATGGAAGTGACGATTGCTAACGAAGTAGTCAA

AAAAGACTTCATTGTGGATTATGGTAATAAATGA

Amino Acid Sequence
(SEQ ID NO: 8)
MRGSHHHHHHGSAEDNQLESASKEEQKGSRDNENSKLNQVDLDNGSHSSE

KTTNVNNATEVKKVEAPTTSDVSKPKANEAVVTNESTKPKTTEAPTVNEE

SIAETPKTSTTQQDSTEKNNPSLKDNLNSSTTSKESKTDEHSTKQAQMS

TNKSNLDTNDSPTQSEKTSSQANNDSTDNQSAPSKQLDSKPSEQKVYKTK

FNDEPTQDVEHTTTKLKTPSVSTDSSVNDKQDYTRSAVASLGVDSNETEA

ITNAVRDNLDLKAASREQINEAIIAEALKKDFSNPDYGVDTPLALNRSQS

KNSPHKSASPRMNLMSLAAEPNSGKNVNDKVKITNPTLSLNKSNNHANNV

IWPTSNEQFNLKANYELDDSIKEGDTFTIKYGQYIRPGGLELPAIKTQLR

SKDGSIVANGVYDKTTNTTTYTFTNYVDQYQNITGSFDLIATPKRETAIK

DNQNYPMEVTIANEWKKDFIVDYGNK
Underlined sequence represents the purification
tag generated from the PQE-30 expression vector.

SdrF N1 (52-361):

Nucleotide Sequence
(SEQ ID NO: 9)
ATGAGAGGATCGCATCACCATCACCATCACGGATCCGCTGAAGACAATCA

ATTAGAATCAGCTTCAAAAGAAGAACAGAAAGGTAGTCGTGATAATGAAA

ACTCAAAACTTAATCAAGTCGATTTAGACAACGGATCACATAGTTCTGAG

AAAACAACAAATGTAAACAATGCAACTGAAGTAAAAAAAGTTGAAGCACC

AACGACAAGTGACGTATCTAAGCCTAAAGCTAATGAAGCAGTAGTGACGA

ATGAGTCAACTAAACCAAAAACAACAGAAGCACCAACTGTTAATGAGGAA

TCAATAGCTGAAACACCCAAAACCTCAACTACACAACAAGATTCGACTGA

GAAGAATAATCCATCTTTAAAAGATAATTTAAATTCATCCTCAACGACAT

CTAAAGAAAGTAAAACAGACGAACATTCTACTAAGCAAGCTCAAATGTCT

ACTAATAAATCAAATTTAGACACAAATGACTCTCCAACTCAAAGTGAGAA

AACTTCATCACAAGCAAATAACGACAGTACAGATAATCAGTCAGCACCTT

CTAAACAATTAGATTCAAAACCATCAGAACAAAAAGTATATAAAACAAAA

TTTAATGATGAACCTACTCAAGATGTTGAACACACGACAACTAAATTAAA

AACACCTTCTGTTTCAACAGATAGTTCAGTCAATGATAAGCAAGATTACA

CACGAAGTGCTGTAGCTAGTTTAGGTGTTGATTCTAATGAAACAGAAGCA

ATTACAAATGCAGTTAGAGACAATTTAGATTTAAAAGCTGCATCTAGAGA

ACAAATCAATGAAGCAATCATTGCTGAAGCACTAAAAAAAGACTTTTCTA

ACCCTGATTATGGTGTCGATACGCCATTAGCTCTAAACAGATCTCAATCA

AAAAATTCACCACATAAGAGTGCAAGTCCACGCATGAATTTAATGAGTTT

AGCTGCTGAGCCTTGA

Amino Acid Sequence
(SEQ ID NO: 10)
MRGSHHHHHHGSAEDNQLESASKEEQKGSRDNENSKLNQVDLDNGSHSSE

KTTNVNNATEVKKVEAPTTSDVSKPKANEAWTNESTKPKTTEAPTVNEES

IAETPKTSTTQQDSTEKNNPSLKDNLNSSSTTSKESKTDEHSTKQAQMST

NKSNLDTNDSPTQSEKTSSQANNDSTDNQSAPSKQLDSKPSEQKVYKTKF

NDEPTQDVEHTTTKLKTPSVSTDSSVNDKQDYTRSAVASLGVDSNETEAI

TNAVRDNLDLKAASREQINEAIIAEALKKDFSNPDYGVDTPLALNRSQSK

NSPHKSASPRMNLMSLAAEP
Underlined sequence represents the purification
tag generated from the PQE-30 expression vector.

SdrF N2 (361-517):
Nucleotide Sequence
(SEQ ID NO: 11)
ATGAGAGGATCGCATCACCATCACCATCACGGATCCCCTAATAGTGGTAA

AAATGTGAATGATAAAGTTAAAATCACAAACCCTACGCTTTCACTTAATA

AGAGTAATAATCACGCTAATAACGTAATATGGCCAACAAGTAACGAACAA

TTTAATTTAAAAGCAAATTATGAATTAGATGACAGCATAAAAGAGGGAGA

TACTTTTACTATTAAGTATGGTCAGTATATTAGACCGGGTGGTTTAGAAC

TTCCTGCAATAAAAACTCAACTACGTAGTAAGGATGGCTCTATTGTAGCT

AATGGTGTATATGATAAAACTACAAATACGACGACTTATACATTTACTAA

CTATGTTGATCAATATCAAAATATTACAGGTAGTTTTGATTTAATTGCGA

CGCCTAAGAGGGAAACAGCAATTAAGGATAATCAGAATTATCCTATGGAA

GTGACGATTGCTAACGAAGTAGTCAAAAAAGACTTCATTGTGGATTATGG

TAATAAATGA

Amino Acid Sequence
(SEQ ID NO: 12)
MRGSHHHHHHGSPNSGKNVNDKVKITNPTLSLNKSNNHANNVIWPTSNEQ

FNLKANYELDDSIKEGDTFTIKYGQYIRPGGLELPAIKTQLRSKDGSIVA

NGVYDKTTNTTTYTFTNYVDQYQNITGSFDLIATPKRETAIKDNQNYPME

VTIANEWKKDFIVDYGNK
Underlined sequence represents the purification tag
generated from the PQE-30 expression vector.

SdrF N3 (517-679):

Nucleotide Sequence
(SEQ ID NO: 13)
ATGAGAGGATCGCATCACCATCACCATCACGGATCCAAAAGGACAATAC

AACTACAGCAGCGGTAGCAAATGTGGATAATGTAAATAATAAACATAACG

AAGTTGTTTATCTAAACCAAAATAACCAAAACCCTAAATATGCTAAATAT

TTCTCAACAGTAAAAAATGGTGAATTTATACCAGGTGAAGTGAAAGTTTA

CGAAGTGACGGATACCAATGCGATGGTAGATAGCTTCAATCCTGATTTAA

ATAGTTCTAATGTAAAAGATGTGACAAGTCAATTTGCACCTAAAGTAAGT

GCAGATGGTACTAGAGTTGATATCAATTTTGCTAGAAGTATGGCAAATGG

TAAAAAGTATATTGTAACTCAAGCAGTGAGACCAACGGGAACTGGAAATG

TTTATACCGAATATTGGTTAACAAGAGATGGTACTACCAATACAAATGAT

TTTTACCGTGGAACGAAGTCTACAACGGTGACTTATCTCAATGGTTCTTC

AACAGCACAGGGGATAATCCTTGA

Amino Acid Sequence
(SEQ ID NO: 14)
MRGSHHHHHHGSKKDNTTTAAVANVDNVNNKHNEWYLNQNNQNPKYAKYF

STVKNGEFIPGEVKVYEVTDTNAMVDSFNPDLNSSNVKDVTSQFAPKVSA

DGTRVDINFARSMANGKKYIVTQAVRPTGTGNVYTEYWLTRDGTTNTNDF

YRGTKSTTVTYLNGSSTAQGDNP
Underlined sequence represents the purification
tag generated from the PQE-30 expression vector.

Protein Production and Purification

Using PCR, the A domain of SdrF (SdrFN1N2N3 representing AA 52-679) was amplified from S. epidermidis K28 genomic DNA (from sequences described above) and subcloned into the E. coli expression vector PQE-30 (Qiagen), which allows for the expression of a recombinant fusion protein containing six histidine residues. Fragments of this A domain, SdrF N2N3, N2 and N3 were also generated (from sequences described above). These vectors were independently transformed into the E. coli strain ATCC 55151, grown in a 15-liter fermentor to an optical density ($OD_{600}$) of 0.7 and induced with 0.2 mM isopropyl-1-beta-D galactoside (IPTG) for 4 hours. The cells were harvested using an AG Technologies hollow-fiber assembly (pore size of 0.45 μm) and the cell paste frozen at −80° C. Cells were lysed in 1×PBS (10 mL of buffer/1 g of cell paste) using 2 passes through the French Press @ 1100 psi. Lysed cells were spun down at 17,000 rpm for 30 minutes to remove cell debris. Supernatant was passed over a 5-mL HITRAP Chelating (Pharmacia) column charged with 0.1M $NiCl_2$. After loading, the column was washed with 5 column volumes of 10 mM Tris, pH 8.0, 100 mM NaCl (Buffer A). Protein was eluted using a 0-100% gradient of 10 mM Tris, pH 8.0, 100 mM NaCl, 200 mM imidazole (Buffer B) over 30 column volumes. SdrFN1N2N3 or SdrFN2N3 eluted at ~13% Buffer B (~26 mM imidazole). Absorbance at 280 nm was monitored. Fractions containing SdrF-N1N2N3, SdrF-N2N3 SdrF-N2 or SdrF-N3 were dialyzed in 1×PBS.

Each protein was put through an endotoxin removal protocol. Buffers used during this protocol were made endotoxin free by passing over a 5-mL MONO-Q SEPHAROSE (Pharmacia) column. Protein was divided evenly between 4×15 mL tubes. The volume of each tube was brought to 9 mL with Buffer A. 1 mL of 10% TRITON X-114 was added to each tube and incubated with rotation for 1 hour at 4° C. Tubes were placed in a 37° C. water bath to separate phases. Tubes were spun down at 2,000 rpm for 10 minutes and the upper aqueous phase from each tube was collected and the detergent extraction repeated. Aqueous phases from the 2nd extraction were combined and passed over a 5-mL IDA chelating (Sigma) column, charged with $0.1M\ NiCl_2$ to remove remaining detergent. The column was washed with 9 column volumes of Buffer A before the protein was eluted with 3 column volumes of Buffer B. The eluant was passed over a 5-mL DETOXIGEL (Sigma) column and the flow-through collected and reapplied to the column. The flow-through from the second pass was collected and dialyzed in 1×PBS. The purified product was analyzed for concentration, purity and endotoxin level before administration into the mice and rabbits

Example 2

Immunization Strategies for Monoclonal Antibody Production

With the goal of generating and characterizing monoclonal antibodies (mAbs), strategies were formulated to generate mAbs against SdrF that were of high affinity, able to interrupt or restrict the binding of ECM proteins to SdrF and demonstrate therapeutic efficacy in vivo.

E. coli expressed and purified SdrF (N1N2N3) protein was used to generate a panel of murine monoclonal antibodies. Briefly, a group of Balb/C mice received a series of subcutaneous immunizations of 1-10 mg of protein in solution or mixed with adjuvant.

Seven days after each boost, serum was collected and titered in ELISA assays against MSCRAMMs or on whole cells (S. epidermidis). Three days after the final boost, the spleen was removed, teased into a single cell suspension and the lymphocytes harvested. The lymphocytes were then fused to a P3X63Ag8.653 myeloma cell line (ATCC #CRL-1580). Cell fusion, subsequent plating and feeding were performed according to the Production of Monoclonal Antibodies protocol from *Current Protocols in Immunology* (Chapter 2, Unit 2).

Example 3

Screening and Selection of Anti-SdrF Monoclonal Antibodies

Hybridomas generated from the fusion were screened for specific anti-SdrF antibody production using a standard ELISA assay. Positive clones were expanded and tested further for activity in a whole bacterial cell binding assay by flow cytometry and SdrF binding by Biacore analysis.

ELISA Analysis

Immulon 2-HB high-binding 96-well microtiter plates (Dynex) were coated with 1 µg/well of SdrF N1N2N3, N2N3, N2 or N3 in 1×PBS, pH 7.4 and incubated for 2 hours at room temperature. All washing steps in ELISAs were performed three times with 1×PBS, 0.05% TWEEN-20 wash buffer. Plates were washed and blocked with a 1% BSA solution at room temperature for 1 hour before hybridoma supernatant samples were added to wells. Plates were incubated with samples and relevant controls such as media alone for one hour at room temperature, washed, and goat anti-mouse IgG-AP (Sigma) diluted 1:5000 in 1×PBS, 0.05% TWEEN-20, 0.1% BSA was used as a secondary reagent. Plates were developed by addition of 1 mg/ml solution of 4-nitrophenyl phosphate (pNPP) (Sigma), followed by incubation at 37° C. for 30 minutes. Absorbance was read at 405 nm using a SPECTRAMAX 190 Plate Reader (Molecular Devices Corp.). Antibody supernatants that had an $OD_{405} \geq 3$ times above background (media alone, ~0.1 OD) were considered positive.

Biacore Analysis

Throughout the analysis, the flow rate remained constant at 10 ml/min. Prior to the SdrFN1N2N3 or SdrFN2N3 injection, test antibody was adsorbed to the chip via RAM-Fc binding. At time O, SdrF (N1N2 or N1N2N3) at a concentration of 30 mg/ml was injected over the chip for 3 min followed by 2 minutes of dissociation. This phase of the analysis measured the relative association and disassociation kinetics of the Mab/SdrF interaction.

Generation of Polyclonal Antiserum Against SdrF

Polyclonal antiserum was generated by Strategic BioSolutions Inc. in New Zealand White SPF Rabbits using a standard immunization schedule. A primary subcutaneous immunization of 200 µg total SdrF protein with Complete Freund's adjuvant was administered on day 0. Boost immunizations of 200 µg total protein with Incomplete Freund's Adjuvant (IFA) were administered on days 21 and 35. The first test bleed was harvested on day 44, followed by an additional boost immunization on day 49, for a total of 4 immunizations. Test bleeds were then collected on days 58 and 63 with a final serum harvest on day 71. The IgG fraction was purified via protein A affinity chromatography and quantitated by OD280 uv-spectroscopy based on an extinction coefficient of 1.33.

Binding to Whole Bacteria in Flow

*Staph.* epi strain (9491) were collected, washed and incubated with mAb or PBS alone (control) at a concentration of 2 mg/ml after blocking with rabbit IgG (50 mg/ml). Following incubation with antibody (mAb and polyclonal), bacterial cells were incubated with Goat-$F_{(ab')2}$-Anti-Mouse-$F_{(ab')2}$-FITC which served as the detection antibody. After antibody labeling, bacterial cells were aspirated through the FACScaliber flow cytometer to analyze fluorescence emission (excitation: 488, emission: 570). For each bacterial strain, 10,000 events were collected and measured. SdrF positive hybridomas were generated from 4 separate fusions (F108-F111). It was unusual to observe that all of the Biacore positive hybridomas were also positive for whole cell bacterial binding by flow cytometry; indicating that the recombinant A domain construct (SdrF N1N2N3) expressed and purified from *E. coli* mirrored the native antigen on the bacterial cell surface.

For further analysis and selection, a N2 reactive candidate, a N3 reactive candidate and a N2N3 reactive candidate, all SdrF ELISA positive, SdrF BIACORE positive with flat (extremely slow) dissociation rates and flow cytometry positive on 9491 *Staph.* epi cells were selected. Table II shows this characterization

TABLE I

SdrF Domain Specific Hybridomas.

| SdrF Clone | SdrF N1N2N3 ELISA | Biacore Antibody Bound | Biacore SdrF bound | Flow S. epi 9491 | ELISA SdrF N2 | ELISA SdrF N3 | ELISA SdrF N2N3 |
|---|---|---|---|---|---|---|---|
| 108-1 | 0.89 | 523.40 | 145.70 | ++ | 0.23 | 0.57 | 0.99 |
| 108-36 | 0.77 | 875.50 | 146.20 | ++ | 0.61 | 0.17 | 0.72 |
| 110-15 | 0.63 | 617.60 | 152.60 | ++ | 0.14 | 0.11 | 0.70 |
| Polyclonal sera | n.d. | n.d. | n.d. | ++ | n.d. | n.d. | n.d. |

++ = All bacterial cells stained
n.d. = not determined

The above analysis in Table I demonstrates that SdrF has immunogenic epitopes that require the N2 and N3 domains linked (110-15) as well as the N2 (108-36) and N3 (108-1) domains alone. The unique globular domains of N2 and N3 as well as the tertiary conformational structure with N2N3, create epitopes for high affinity interaction with monoclonal antibodies on purified recombinant protein as well as on bacterial cells as demonstrated in Table I. Antibodies recognizing the N1 domain were also generated (data not shown). The flow analysis of cell surface bacterial cell staining demonstrated that the anti-SdrF monoclonals and polyclonal antisera stained with equal intensity and frequency for the greater than 20 S. epidermidis strains tested.

Example 4

Binding Kinetics of Cloned Anti-SdrF Monoclonal Antibodies

Kinetic analysis was performed to demonstrate the diversity of the anti-SdrF mAbs chosen and characterized. As shown below the mAbs differ in there on-rate and off-rate as well as the overall affinity.

Biacore Kinetics

Kinetic analysis was performed on a Biacore 3000 using the ligand capture method included in the software. A GAH-F(ab)$_2$ chip. The anti-SdrF mAbs were then passed over a GAM-F(ab)$_2$ chip, allowing binding to the Fc portion. Varying concentrations of the SdrF (N1N2N3) protein were then passed over the chip surface and data collected. Using the Biacore provided Evaluation software (Version 3.1), $k_{on}$ and $k_{off}$ were measured and $K_A$ and $K_D$ were calculated.

This analysis Table II suggests that the SdrF epitopes of the N2, N3 and N2N3 domains of the A domain are capable of generating high affinity monoclonal antibodies.

Example 5

Cloning, Sequence Characterization and Humanization of 108-1, 108-36 and 110-15

The variable light and heavy chains of the anti-SdrF monoclonals, 108-1, 108-36 and 100-15 were cloned and sequenced to derive a predicted amino acid sequence in the following manner: Briefly, 1.4×10$^8$ hybridoma cells cultured in DMEM-10 medium with 10% FBS were washed with PBS, pelleted by centrifugation then lysed in detergent containing Protein/RNase Degrader. PolyA$^+$ mRNA was isolated by affinity purification on oligo-dT cellulose. Synthesis of first strand cDNA was accomplished using 5? g of mRNA and reverse transcriptase in a cDNA synthesis kit (Novagen; cat #69001-3) containing 20 pmol of 3' oligonucleotide mouse-specific primers (Novagen; cat#69796 and 69812) for each variable heavy and variable light chain. A portion (5 to 50 ng) of the cDNA was amplified by the polymerase chain reaction (PCR) using the PCR Reagent System (Life Technologies; cat#10198-018) and a mouse variable heavy and light chain specific primer set (Novagen; cat#70081-3, 5 pmol each) for 30 cycles (94 C hot start then cycles of 94 C for 1 min, 50 C for 1 min and 72 C for 1 min). PCR products were fractionated electrophoretically in a 1% ultra pure agarose gel in sodium acetate buffer and visualized by ethidium bromide staining. PCR fragments matching the predicted size were excised from the gel and purified using BIO 101 Geneclean spin columns (cat #1101-400) for ligation into the pCR2.1-TOPO (Invitrogen) plasmid, followed by transformation into competent TOP10 E. coli. (Invitrogen; cat#K4500). After isolating plasmid DNA using QIAprep Spin Miniprep Kit (QIAGEN; cat#27106), positive clones with inserts were identified by restriction endonuclease digestion and agarose gel electrophoresis, followed by sequencing on an ABI automated sequencer using M13 Forward and M13 Reverse primers.

TABLE II

Kinetic Analysis using the Biacore

| mAb | Reactive Sub-Domain | $k_a$ Association Rate; msec$^{-1}$ | $k_d$ Disassociation Rate; sec$^{-1}$ | $K_A$ Affinity Constant; M$^{-1}$ | $K_D$ Disassociation Constant; M |
|---|---|---|---|---|---|
| 108-1 | N3 | $8.29 \times 10^4$ | $1.34 \times 10^{-4}$ | $6.20 \times 10^8$ | $1.61 \times 10^{-9}$ |
| 108-36 | N2 | $2.32 \times 10^5$ | $5.60 \times 10^{-5}$ | $4.52 \times 10^9$ | $2.21 \times 10^{-10}$ |
| 110-15 | N2N3 | $2.12 \times 10^5$ | $1.64 \times 10^{-4}$ | $1.29 \times 10^9$ | $7.74 \times 10^{-10}$ |

108-1VL-Mouse (variable light sequence DNA)
(SEQ ID NO: 15)
GACATTGTGATGACCCAGTCTCACAAATTCATGTCCACATCAGTAGGAGA

CAGGGTCATCATCACCTGCAAGGCCAGTCAGGATGTGAATACTGCTCTAG

CCTGGTATCAGCAGAAACCAGGACAATCTCCTAAACTACTGATTTACTCG

GCATCCTACCGGTATACTGGAGTCCCTGATCGCTTCACTGGCAGTGGATC

TGGGACGGATTTCACTTTCACCATCAGCAGTGTGCAGGCTGAAGACCTGG

CAGTTTATTACTGTCAGCAACATTATAGTACCCCTCCGTACACGTTCGGA

GGGGGGACCAAGCTGGAGATAAAA 108-1VL-Mouse (variable light sequence)
(SEQ ID NO: 16)
DIVMTQSHKFMSTSVGDRVIITC<u>KASQDVNTALA</u>WYQQKPGQSPKLLIY<u>S ASYRYT</u>GVPDRFTGSGSGTDFTFTISSVQAEDLAVYYC<u>QQHYSTPPYT</u>FG GGTKLEIK
Amino acids representing a CDR are underlined.

108-1VH-Mouse (variable heavy sequence DNA)
(SEQ ID NO: 17)
GAGGTTCAGCTGCAGCAGTCTGGGGCAGAGCTTGTGAAGCCAGGGGCCTC

AGTCAAGTTGTCCTGCACAGCTTCTGGCTTCAACATTAAAGACACCTATA

TACACTGGGTGAAGCAGAGGCCTGAACAGGGCCTGGAGTGGATTGGAAGG

ATTGATCCTGCGAATGGTAATACTCATTATGACTCACAGTTCCAGGGCAA

GGCCACTATAACAGCAGACACATCCTCCAACACAGCCTACCTGCAGCTCA

GCAGCCTGACATCTGACGACACTGCCGTCTATTACTGTACTAGACGTGTG

GGCTATGCTATGGACTACTGGGGTCAAGGAACCTCAGTCACCGTCTCCTC

A 108-1VH-Mouse (variable heavy sequence)
(SEQ ID NO: 18)
EVQLQQSGAELVKPGASVKLSCTASGFNIK<u>DTYIH</u>WVKQRPEQGLEWIG<u>R IDPANGNTHYDSQFQGK</u>ATITADTSSNTAYLQLSSLTSDDTAVYYCTR<u>RV GYAMDY</u>WGQGTSVTVSS
Amino acids representing a CDR are underlined.

108-36VL-Mouse (variable light sequence DNA)
(SEQ ID NO: 19)
CAAATTGTTCTCACCCAGTCTCCAGCAATCATGTCTGCATCTCCAGGGGA

GAAGGTCACCATGACCTGCAGTGCCAGCTCAAGTGTAAGTTACATGTACT

GGTACCAACAGAAACCAGGATCCTCCCCCAGAGTCCTGATTTATGACACA

TCCAACCTGGCTTCTGGAGTCCCTGTTCGCTTCAGTGGCAGTGGGTCTGG

GACCTCTTACTCTCTCACAATCAGCCGAATGGAGGCTGAAGATGCTGCCA

CTTATTACTGCCAGCAGTGGAATGGTTATCCACCCACGTTCGGTGCTGGG

ACCAAGCTGGAGGTGAAA 108-36VL-Mouse (variable light sequence)
(SEQ ID NO: 20)
QIVLTQSPAIMSASPGEKVTMTC<u>SASSSVSYMY</u>WYQQKPGSSPRVLIY<u>DT SNLAS</u>GVPVRFSGSGSGTSYSLTISRMEAEDAATYYC<u>QQWNGYPPT</u>FGAG TKLEVK
Amino acids representing a CDR are underlined.

108-36VH-Mouse (variable heavy sequence DNA)
(SEQ ID NO: 21)
CAGGTTACTCTGAGAGAGTCTGGCCCTGGGATATTGCAGCCCTCCCAGAC

CCTCAGTCTGACTTGTTCTTTCTCTGGGTTTTCACTGAACACTTCTGGTA

TGGGTGTGACCTGGATTCGTCAGCCTTCTGGAAAGGGTCTGGAGTGGCTG

GCAAACATTTACTGGGATGATGACAAGCGCTATAACCCATCCCTGAAGAG

CCGGCTCACAATCTCCAAGGCTAACTCCAGAAACCAGGTATTCCTCAAGA

TCACCAGTGTGGACACTGCAGATACTGCCACATACTACTGTACTCGCCCC

AATTACCTCGGTACTGTCTACTGGTACTTTGATGTCTGGGGCGCAGGGAC

CATGGTCACCGTCTCCTCA 108-36VH-Mouse (variable heavy sequence)
(SEQ ID NO: 22)
QVTLRESGPGILQPSQTLSLTCSFSGFSLN<u>TSGMGVT</u>WIRQPSGKGLEWL G<u>ANIYWDDDKRYNPSLKS</u>RLTISKANSRNQVFLKITSVDTADTATYYCTR<u>P NYLGTVYWYFDV</u>WGAGTMVTVSS
Amino acids representing a CDR are underlined.

110-15VL-Mouse (variable light sequence DNA)
(SEQ ID NO: 23)
CAAATTGTTCTCACCCAGTCTCCAGCAATCATGTCTGCATCTCCAGGGGA

GGAGGGCACCATGACCTGCAGTGCCAGCTCAAGTGTAAGGTACATGTACT

GGTACCGGCAGAAGCCAGGATCCTCCCCCAGACTCTTGATTTATGACACA

TCCAACCTGGCTTCTGGAGTCCGTGTTCGCTTCAGTGGCAGTGGGTCTGG

GACCTCTTACTCTCTCACAATCAGCCGAATGGAGGCTGAAGATGCTGCCA

CTTATTACTGCCAGCAGTGGAGTAGTTACCCACCCACGTTCGGAGGGGGG

ACCAAGCTGGAAATGAAA 110-15VL-Mouse (variable light sequence)
(SEQ ID NO: 24)
QIVLTQSPAIMSASPGEEGTMTC<u>SASSSVRYMY</u>WYRQKPGSSPRLLIY<u>DT SNLAS</u>GVPVRFSGSGSGTSYSLTISRMEAEDAATYYC<u>QQWSSYPPT</u>FGGG TKLEMK
Amino acids representing a CDR are underlined.

110-15VH-Mouse (variable heavy sequence DNA)
(SEQ ID NO: 25)
GAAGTGCAGTTGGTGGAGTCTGGGGGAGGCTTAGTGAAGCCTGGAGGGTC

CCTGAAACTCTCCTGTGCAGCCTCTGGATTCGCTTTCAGTAGCTATGACA

TGTCTTGGGTTCGCCAGACTCCGGAGAAGAGGCTGGAGTGGGTCGCCTAC

ATTAGTAGTGGTGGTGGTATCACCTACTATCCAGACACTGTGAAGGGCCG

ATTCACCATCTCCAGAGACAATGCCAAGAACACCCTGTACGTGCAAATGA

GCAGTCTGAAGTCTGAGGACACAGCCATTTATTATTGTACAAGACACGAT

AGGGACTCCTGGTTTGCTTATTGGGGCCAAGGGACTCTGGTCACTGTCTC

TGCA 110-15VH-Mouse (variable heavy sequence)
(SEQ ID NO: 26)
EVQLVESGGGLVKPGGSLKLSCAASGFAFS<u>SYDMS</u>WVRQTPEKRLEWVA<u>Y ISSGGGITYYPDTVKGR</u>FTISRDNAKNTLYVQMSSLKSEDTAIYYCTR<u>HD RDSWFAY</u>WGQGTLVTVSA
Amino acids representing a CDR are underlined.

The process of humanization outlined in this disclosure focuses on changing only the solvent exposed residues of the mouse variable regions that are not involved in the molecule's specificity and affinity for the ClfA target antigen. The information for these determinations utilized solvent availability determinations published by Padlan (A possible procedure for reducing the immunogenicity of antibody variable domains while preserving their ligand binding properties. Molecular Immunology, 28(4); 489-498, 1991). Importantly, molecular modeling in silico or algorithms to determine T-cell epitopes were not used to make these determinations.

The approach represents a process by which the mouse variable region residues of the light and heavy chain are changed by site directed mutagenesis to reflect the surface exposed architecture of the most homologous human variable region from the public database. Specifically, the amino acids defining the variable heavy and light chains were assigned a Kabot position number and "exposure" designation based on Padlan (see, e.g., references cited above), allowing the alignment of the amino acids from each human framework subgroup (I-III for the heavy chain and I-IV for the light chain). To support this analysis, a BLAST search was carried out on the human immunoglobulin database as well as the entire protein database where the variable region with the highest homology to the mouse sequence (both germ-line and mature) were chosen and aliened with the murine sequence of interest. Once aliened, the human subgroup with the highest homology to the mouse sequence was identified. The exposed mouse amino acid residues were mutated to mimic the most homologous human subgroup. In cases were there was more than one amino acid found in the subgroup at that position, the amino acid represented in the human germ line sequence with the highest homology to the mouse sequence was used. These changes were incorporated into de novo synthesized (Blue Heron Biotechnology: Bothell, Wash.) gene sequences representing the variable light and heavy chain coding regions then spliced in frame into plasmids that contain the appropriate light or heavy chain constant region. Isolated plasmid DNA was transfected into NS0 cells via electroporation, clones selected by limiting dilution and mAb purified from scaled-up supernatant for characterization.

```
108-1VL-Hu (humanized variable light sequence)
                                     (SEQ ID NO: 27)
DIVMTQSQKFMSTSVGDRVTITCKASQDVNTALAWYQQKPGQSPKLLIYS

ASYRYTGVPSRFSGSGSGTDFTFTISSVQAEDLAVYYCQQHYSTPPYTFG

GGTKLEIK
Amino acids representing a CDR are underlined,
amino acids in bold represent humanization changes
(4).

108-1VH-Hu (humanized variable heavy sequence)
                                     (SEQ ID NO: 28)
QVQLVQSGAEVVKPGASVKLSCKASGFNIKDTYIHWVKQRPGQGLEWIGR

IDPANGNTHYDSQFQGKATITADTSTSTAYLQLSSLRSEDTAVYYCTRRV

GYAMDYWGQGTTVTVSS
Amino acids representing a CDR are underlined,
amino acids in bold represent humanization changes
(10).

108-36VL-Hu (humanized variable light sequence)
                                     (SEQ ID NO: 29)
EIVLTQSPATMSASPGERVTMSCSASSSVSYMYWYQQKPGQSPRVLIYDT

SNLASGVPSRFSGSGSGTSYSLTISSMEPEDAATYYCQQWNGYPPTFGGG

TKLEVK
Amino acids representing a CDR are underlined,
amino acids in bold represent humanization changes
(9).

108-36VH-Hu (humanized variable heavy sequence)
                                     (SEQ ID NO: 30)
QVTLRESGPGILKPSQTLSLTCTFSGFSLNTSGMGVTWIRQPSGKGLEWL

ANIYWDDDKRYNPSLKSRLTISKANSRNQVFLKITSVDPVDTATYYCTRP

NYLGTVYWYFDVWGQGTMVTVSS
Amino acids representing a CDR are underlined,
amino acids in bold represent humanization changes
(5).

110-15VL-Hu (humanized variable light sequence)
                                     (SEQ ID NO: 31)
EIVLTQSPGTMSASPGERGTMSCSASSSVRYMYWYRQKPGQSPRLLIYDT

SNLASGVPARFSGSGSGTSYSLTISRMEAEDAATYYCQQWSSYPPTFGGG

TKLEMK
Amino acids representing a CDR are underlined,
amino acids in bold represent humanization changes
(7).

110-15VH-Hu (humanized variable heavy sequence)
                                     (SEQ ID NO: 32)
EVQLVESGGGLVQPGGSLKLSCAASGFAFSSYDMSWVRQTPEKRLEWVAY

ISSGGGITYYPDTVKGRFTISRDNSKNTLYVQMSSLRAEDTAVYYCTRHD

RDSWFAYWGQGTLVTVSS
Amino acids representing a CDR are underlined,
amino acids in bold represent humanization changes
(6).
```

Example 6

Effect of Humanization on Affinity

To determine the effect of the humanization process on the specific binding affinity of 108-1, 108-36 and 110-15 for SdrF (N1N2N3), affinities of the mouse and humanized antibodies were compared.

Affinity Measurement by Biacore

Kinetic analysis was performed on a Biacore 3000 (Biacore, Piscataway, N.J.) using the ligand capture method included in the software. The anti-SdrF mAbs were passed over a Goat anti-mouse-F(ab)$_2$ chip, allowing binding and capture via the Fc portion. Varying concentrations of the SdrF (N1N2N3) protein were then passed over the chip, and data collected. Using the Biacore provided Evaluation software (Version 3.1); $k_{on}$ and $k_{off}$ were measured and $K_A$ and $K_D$ were calculated.

TABLE III

Affinity Comparison Before and After Humanization.

| mAb | $k_a$ (M$^{-1}$s$^{-1}$) | $k_d$ (s$^{-1}$) | $K_A$ (M$^{-1}$) | $K_D$ (M) |
|---|---|---|---|---|
| Murine 108-1 | $8.3 \times 10^4$ | $1.3 \times 10^{-4}$ | $6.2 \times 10^8$ | $1.6 \times 10^{-9}$ |
| Humanized 108-1 | $9.4 \times 10^4$ | $1.7 \times 10^{-4}$ | $5.6 \times 10^8$ | $1.8 \times 10^{-9}$ |
| Murine 110-15 | $2.1 \times 10^5$ | $1.6 \times 10^{-4}$ | $1.3 \times 10^8$ | $7.7 \times 10^{-10}$ |
| Humanized 110-15 | $1.7 \times 10^5$ | $1.3 \times 10^{-4}$ | $1.4 \times 10^9$ | $7.4 \times 10^{-10}$ |
| Murine 108-36 | $2.3 \times 10^5$ | $5.6 \times 10^{-5}$ | $4.5 \times 10^9$ | $2.2 \times 10^{-10}$ |
| Humanized 108-36 | $1.4 \times 10^5$ | $6.3 \times 10^{-5}$ | $2.2 \times 10^9$ | $4.6 \times 10^{-10}$ |

The humanization process outlined in Example 5 preserved the original affinity of the starting mouse immunoglobulin (Table III).

Example 7

OP Activity of SdrF Coated Beads with a Monoclonal Against SdrF

To determine the relationship between SdrF epitope specificity and immunoglobulin effector function, experiments were designed to characterize opsonophagocytic activity measuring HL 60 phagocytic cell uptake of SdrF antigen coated beads.
Opsonophagocytic Activity (OP Uptake) with SdrF-Coated Fluorescent Beads and HL60 Effector Cells SdrF antigen-coated fluorescent beads (1 μm diameter, Polysciences, Inc., Warrington, Pa.) were opsonized with increasing concentrations of anti-SdrF mAb or a negative control antibody (anti-ACE40). Sterile baby rabbit serum (Cedarlane Labs Ltd., Hornby, Ontario, Canada) was added as a source of complement. The opsonized fluorescent microspheres were incubated with a human phagocytic cell line (HL-60).

The assay was performed by preparing stock IgG solutions at 100 μg/ml followed by serial 2 fold dilutions in Gelatin Veronal Buffer with $Ca^{2+}$ and $Mg^{2+}$ (GVB) (Sigma-Aldrich, Inc., Cat. #G6514). 10 μl of the IgG dilutions were added to a 96 well tissue culture plate (Corning Inc., Corning N.Y.). 1:500 dilution of the SdrF coated beads was prepared resulting in approximately $2-4\times10^7$ beads/ml. 20 μl of the diluted bead suspension was added to the wells of the plate. The resulting beads—antibodies mixture was incubated at 37° C. for 30 minutes at 250 rpm. At the end of incubation 10 μl of 1:8 baby rabbit complement dilution in GVB was added to each well of the 96-well plate. The plate was incubated for 15 min at 37° C. at 250 rpm. 40 μl of HL60's cell suspension was then added to the wells of the 96-well plate. The plate was incubated for 30 minutes at 37° C. and at 250 rpm. Following the 30 min incubation, 80 μl of cold GVB buffer added to each well of the plate. The level of opsonic activity was measured by flow cytometry as the percentage of fluorescent phagocytic cells.

The results displayed in FIG. 1 demonstrate OP activity with a humanized anti-SdrF monoclonal when mixed in the presence of SdrF coated beads and complement. The Hu108-36 mAb recognizes an epitope on the N2 portion of the SdrF molecule that facilitates bead uptake by HL60 cells as the mAb concentration is increased. Control mAb (anti-Ace40) has no effect on bead uptake.

Example 8

Mutagenesis of Hu108-36 Removes an N-Linked Carbohydrate Chain from the Variable Heavy Chain Region to Increase Binding to SdrF By sequence and biochemical analysis, an N-linked carbohydrate chain was identified linked to the asparagine at position 30 of the variable heavy chain of Hu108-36. Substitution of this amino acid to serine by de novo gene synthesis (Blue Heron Biotechnology; Bothell, Wash.) then spliced in frame into plasmids that contain the appropriate light or heavy chain constant region. Isolated plasmid DNA was transfected into NS0 cells via electroporation, supernatant harvested after seven days, quantified by HPLC protein A capture and analyzed by Biacore.

108-36VH-Hu (humanized variable heavy DNA sequence) N→S
(SEQ ID NO: 33)
CAGGTTACTCTGAGAGAGTCTGGCCCTGGGATATTGAAGCCCTCCCAGAC

CCTCAGTCTGACTTGTACCTTCTCTGGGTTTTCACTGAGCACTTCTGGTA

TGGGTGTGACCTGGATTCGCCAGCCTTCTGGAAAGGGTCTGGAGTGGCTG

GCAAACATTTACTGGGATGATGACAAGCGCTATAACCCATCCCTGAAGAG

CCGGCTCACAATCTCCAAGGCTAACTCCAGAAACCAGGTGTTCCTCAAGA

TCACCAGTGTGGACCCCGTGGATACTGCCACATACTACTGTACTCGCCCC

AATTACCTGGGTACTGTGTACTGGTACTTTGATGTCTGGGGCCAGGGGAC

CATGGTGACCGTGTCCTCA
Changed codon is highlighted in bold print.

108-3BVH-Hu (humanized variable heavy protein sequence) N→S
(SEQ ID NO: 34)
QVTLRESGPGILKPSQTLSLTCTFSGFSL<u>STSGMGVT</u>WIRQPSGKGLEWL A<u>NIYWDDDKRYNPSLKSR</u>LTISKANSRNQVFLKITSVDPVDTATYYCTR<u>P NYLGTVYWYFDVWGQGTMVTVSS</u>
Amino acids representing a CDR are underlined, amino acid in bold represents the asparagine to serine change.

Figure 2:
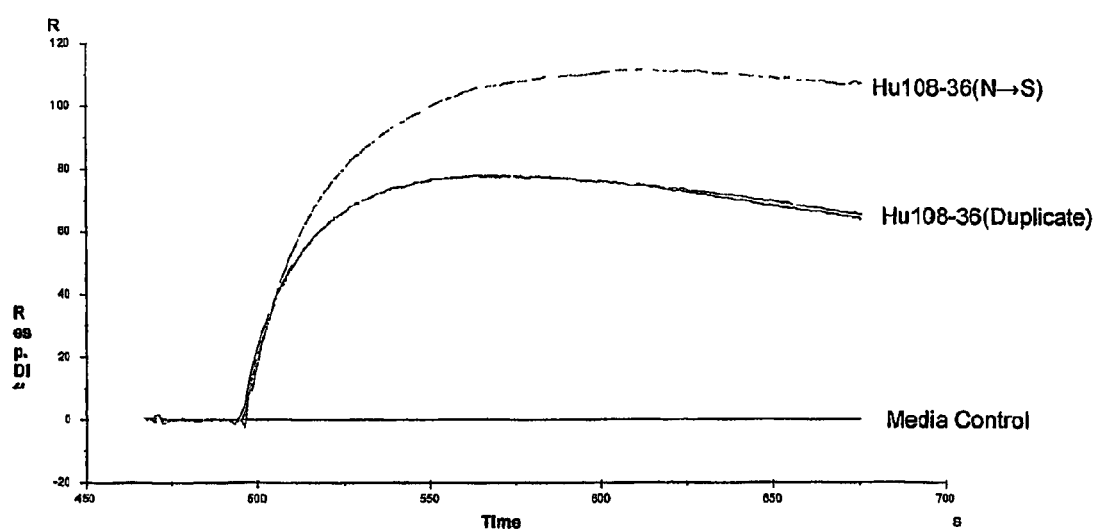
FIG. 2 is a graphic representation of the biacore capture/binding of SdrF with Hu108-36 and Hu108-36 (N→S)

The kinetics curve in FIG. 2 demonstrates that replacement of the asparagine with a serine (thereby removing the N-linked carbohydrate moiety from position 30 of the variable heavy chain) slowed the off-rate of SdrF capture. These results demonstrate that the overall affinity of Hu108-36 has been improved by this process.

Example 9

Protective Effects of Anti-SdrF Antibodies In Vivo

The protective value of antibodies against the SdrF target on the bacterial cell surface was evaluated in a rodent model of S. epidermidis infection using the monoclonals described above and polyclonal antiserum to SdrF obtained as described below.
Generation of Polyclonal Antiserum Against SdrF Polyclonal antiserum was generated by Strategic BioSolutions Inc. in New Zealand White SPF Rabbits using a standard immunization schedule. A primary subcutaneous immunization of 200 μg total SdrF protein with Complete Freund's adjuvant was administered on day 0. Boost immunizations of 200 μg total protein with Incomplete Freund's Adjuvant (IFA) were administered on days 21 and 35. The first test bleed was harvested on day 44, followed by an additional boost immunization on day 49, for a total of 4 immunizations. Test bleeds were then collected on days 58 and 63 with a final serum harvest on day 71. The IgG fraction was purified via protein A affinity chromatography and quantitated by OD280 uv-spectroscopy based on an extinction coefficient of 1.33.
Rodent Model of S. epidermidis Infection The rodent model was performed in accordance with the institutional policies of Inhibitex, Inc. Pregnant Wistar-Hannover rats were purchased from Charles River Laboratories (Wilmington, Mass.). Three- to six-day-old newborn rats (7 to 11 g) were injected intraperitoneally (i.p.) with 1.6 mg or 0.8 mg of protein A purified rabbit anti-SdrF polyclonal antibody, anti-SdrF monoclonal antibody or an equal volume of buffer (n=12). To prepare bacteria for challenge, S. epidermidis strain 771-233 cultures were incubated at 37° C. with shaking until mid-log phase (4 hours). The cultures were centrifuged, and the pellets were resuspended in ice cold 1×PBS. Twenty hours after antibody administration, the rats were challenged with an i.p. injection of approximately 1×10$^9$ CFU, and survival was monitored for 3-7 days. Statistical analyses were performed using GraphPad Prism version 4.00 for Windows (GraphPad Software, San Diego, Calif.). Survival fractions were calculated using the product limit method (Kaplan-Meier), and the resulting curves were compared for significance using the Mantel-Haenszel log rank test.

Figure 3:
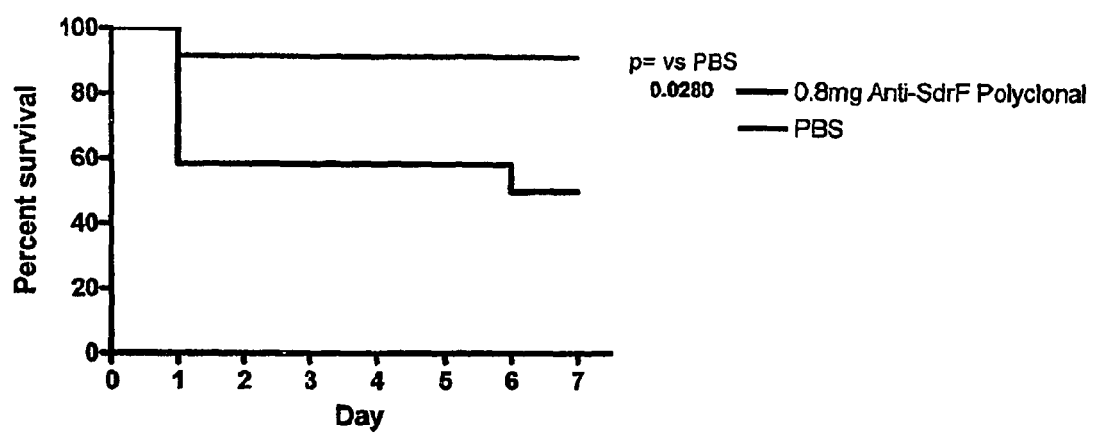
FIG. 3 is a graphic representation of the antibody mediated survival after challenge with *S. epidermidis* 771-233 in a Neonatal Rat model.
Figure 4:
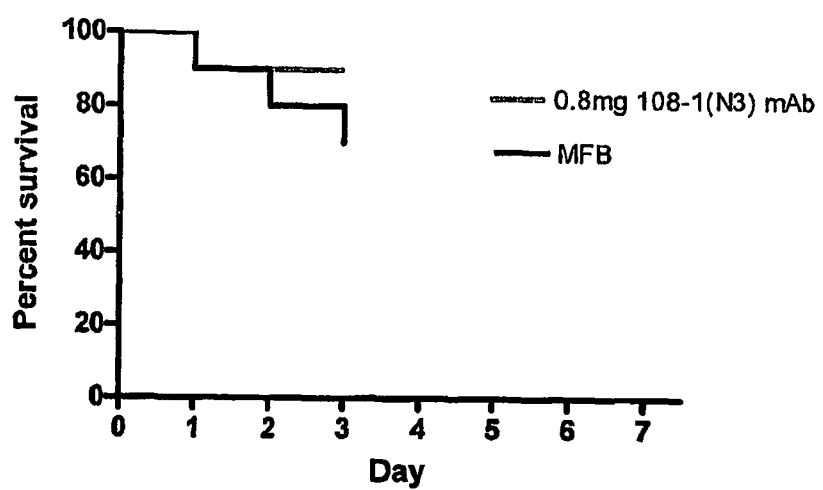
FIG. 4 is a graphic representation of anti-SdrF monoclonal antibody-mediated survival after challenge with *S. epidermidis* 771-233 in a Neonatal Rat model.

The results of these tests on polyclonal and monoclonal antibodies to SdrF are shown in FIGS. 3 and 4, respectively. As shown in FIG. 3 and FIG. 4, the results demonstrate that in addition to the protection afforded by polyclonal antibodies, the monoclonal antibodies against SdrF in accordance with the present invention were able to protect against a *S. epidermidis* challenge in a clinically relevant way.

What is claimed is:

1. An isolated monoclonal antibody which binds specifically to the SdrF protein of *Staphylococcus epidermidis* and which has a variable light chain selected from the group consisting of SEQ ID NO: 16, SEQ ID NO: 20, SEQ ID NO: 24, SEQ ID NO: 27, SEQ ID NO: 29 and SEQ ID NO: 31.

2. The monoclonal antibody according to claim 1 wherein the antibody is raised against the N1N2N3 subregion of the SdrF protein.

3. The monoclonal antibody according to claim 1 wherein the monoclonal antibody is raised against a peptide selected from the group consisting of an antigenic subregion of the SdrF protein, the SdrF ligand binding A domain, the N1 subregion, the N2 subregion, the N3 subregion, and combinations of said subregions.

4. The monoclonal antibody according to claim 1, wherein said antibody is suitable for parenteral, oral, intranasal, subcutaneous, aerosolized or intravenous administration in a human or animal.

5. The monoclonal antibody according to claim 1 wherein the monoclonal antibody is selected from the group consisting of murine, chimeric, humanized and human monoclonal antibodies.

6. The monoclonal antibody according to claim 1 wherein the antibody is a single chain monoclonal antibody.

7. The monoclonal antibody according to claim 1 that is raised against a peptide having the amino acid sequence selected from the group consisting of SEQ ID NO:2, SEQ ID NO:4, SEQ ID NO:6, SEQ ID NO:8, SEQ ID NO:10, SEQ ID NO:12, and SEQ ID NO:14.

8. The monoclonal antibody according to claim 1 wherein the monoclonal antibody recognizes a peptide selected from the group consisting of an antigenic subregion of the SdrF protein, the SdrF ligand binding A domain, the N1 subregion, the N2 subregion, the N3 subregion, and combinations of said subregions.

9. The monoclonal antibody according to claim 1 that recognizes a peptide having the amino acid sequence selected from the group consisting of SEQ ID NO:2, SEQ ID NO:4, SEQ ID NO:6, SEQ ID NO:8 and SEQ ID NO:10 and SEQ ID NO:12, and SEQ ID NO:14.

10. Isolated antisera containing the antibody according to claim 1.

11. A pharmaceutical composition comprising an effective amount of the antibody of claim 1 and a pharmaceutically acceptable vehicle, carrier or excipient.

12. The pharmaceutical composition according to claim 11 further comprising a physiologically acceptable antibiotic.

13. An isolated monoclonal antibody which binds specifically to the SdrF protein of *S. epidermidis*, wherein said antibody has a variable heavy chain selected from the group consisting of SEQ ID NO: 18, SEQ ID NO: 22, SEQ ID NO: 26, SEQ ID NO: 28, SEQ ID NO: 30, SEQ ID NO: 32 and SEQ ID NO: 34.

14. A method of detecting *S. epidermidis* in a sample from a patient infected with *S. epidermidis* comprising adding the monoclonal antibody of claim 1 to the sample and determining the specific binding of the antibody.

15. A method of making the monoclonal antibody of claim 1 comprising administering to a host animal an immunogenic amount of a peptide selected from the group consisting of an antigenic subregion of the SdrF protein, the SdrF ligand binding A domain, the N1 subregion, the N2 subregion, the N3 subregion, and combinations of said subregions, forming a hybridoma, and isolating the monoclonal antibody from said hybridoma.

16. A kit comprising the monoclonal antibody of claim 1 and means for detecting specific binding by said antibody.

17. The kit of claim 16, wherein said means for detecting the binding comprises a detectable label that is linked to said antibody.

* * * * *